US010392626B1

(12) United States Patent
Ahrens et al.

(10) Patent No.: US 10,392,626 B1
(45) Date of Patent: Aug. 27, 2019

(54) PLANT REGULATORY ELEMENTS AND USES THEREOF

(71) Applicant: MONSANTO TECHNOLOGY LLC, St. Louis, MO (US)

(72) Inventors: Jeffrey E. Ahrens, Fenton, MO (US); Paul J. Loida, Kirkwood, MO (US); Elena A. Rice, Olivette, MO (US); J. Philip Taylor, Saint Peters, MO (US); Rebecca L. Thompson, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 559 days.

(21) Appl. No.: 14/511,095

(22) Filed: Oct. 9, 2014

Related U.S. Application Data

(60) Provisional application No. 61/888,972, filed on Oct. 9, 2013.

(51) Int. Cl.
*C12N 15/82* (2006.01)

(52) U.S. Cl.
CPC ..... *C12N 15/8209* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 5,627,061 A | 5/1997 | Barry et al. | |
| 6,196,636 B1 | 3/2001 | Mills et al. | |
| 6,248,876 B1 | 6/2001 | Barry et al. | |
| 6,399,861 B1 | 6/2002 | Anderson et al. | |
| 6,417,428 B1 | 7/2002 | Thomashow et al. | |
| 6,777,589 B1 | 8/2004 | Lundquist et al. | |
| 7,135,616 B2 | 11/2006 | Heard et al. | |
| 7,511,190 B2 | 3/2009 | Sherman et al. | |
| 7,674,955 B2 | 3/2010 | Chan et al. | |
| 8,895,818 B2 | 11/2014 | Chomet et al. | |
| 2003/0121070 A1 | 6/2003 | Adam et al. | |
| 2004/0019925 A1 | 1/2004 | Heard et al. | |
| 2004/0019927 A1 | 1/2004 | Sherman et al. | |
| 2004/0216190 A1 | 10/2004 | Kovalic | |
| 2005/0160493 A9* | 7/2005 | Ratcliffe | C07K 14/415 800/281 |
| 2005/0283856 A1 | 12/2005 | Conner et al. | |
| 2006/0179511 A1 | 8/2006 | Chomet et al. | |
| 2007/0054278 A1 | 3/2007 | Cargill | |
| 2007/0214517 A1 | 9/2007 | Alexandrov et al. | |
| 2008/0127365 A1 | 5/2008 | Sanz Molinero et al. | |
| 2008/0313756 A1 | 12/2008 | Zhang et al. | |
| 2009/0158452 A1 | 6/2009 | Johnson et al. | |
| 2009/0205085 A1 | 8/2009 | Goldman et al. | |
| 2010/0083402 A1 | 4/2010 | Heard et al. | |
| 2010/0162427 A1 | 6/2010 | Riechmann et al. | |
| 2010/0218278 A1 | 8/2010 | Kaster, Jr. et al. | |
| 2010/0313299 A1* | 12/2010 | Sanz Molinero | C12N 15/8261 800/278 |
| 2011/0138499 A1 | 6/2011 | Zhang et al. | |
| 2011/0252501 A1 | 10/2011 | Abad et al. | |
| 2012/0137382 A1 | 5/2012 | Repetti et al. | |
| 2012/0276074 A1 | 11/2012 | Scharenberg et al. | |
| 2015/0047069 A1 | 2/2015 | Chomet et al. | |
| 2015/0052633 A1* | 2/2015 | Creelman | C07K 14/415 800/282 |
| 2015/0101076 A1 | 4/2015 | Adams et al. | |
| 2017/0088904 A1 | 3/2017 | Adams et al. | |

FOREIGN PATENT DOCUMENTS

| | | |
|---|---|---|
| CA | 2456979 | 6/2014 |
| CN | 1933723 | 3/2007 |
| CN | 100999549 | 12/2010 |
| CN | 102154321 | 8/2011 |
| EP | 1797754 | 10/2010 |
| WO | WO 2002/15675 | 2/2002 |
| WO | WO 2002/016655 | 2/2002 |
| WO | WO 2002/016655 | 2/2003 |
| WO | WO 2003/013227 | 2/2003 |
| WO | WO 2003/013228 | 2/2003 |
| WO | WO 2005/059103 | 6/2005 |
| WO | WO 2006/069017 | 6/2006 |
| WO | WO 2006/130156 | 12/2006 |
| WO | WO 2007/023190 | 3/2007 |

(Continued)

OTHER PUBLICATIONS

Ait-ali et al (Flexible control of plant architecture and yield via switchable expression of *Arabidopsis gai*. Plant Biotechnology Journal, 1: 337-343, 2003).*
Reynolds et al (Achieving yield gains in wheat. Plant, Cell and Environment. 35, 1799-1823, 2012).*
U.S. Appl. No. 15/289,635, filed Oct. 10, 2016, Adams et al.
Response to Non-Final Office Action regarding U.S. Appl. No. 14/511,107, dated Oct. 3, 2016.
USPTO: Non-Final Office Action regarding U.S. Appl. No. 14/511,107, dated Jun. 16, 2016.
Chan etal., "Homeoboxes in plant development," *Biochimica et Biophysica Acta* 1442:1-19, 1998.
Cranston et al., "Dicamba resistance in kochia," *Weed Science* 49(2):164-170, 2001.
Oh et al., "Transcriptional regulation of secondary growth in *Arabidopsis thaliana,*" *Journal of Experimental Botany* 54(393):2709-2722, 2003.

(Continued)

*Primary Examiner* — Medina A Ibrahim
*Assistant Examiner* — Wayne Zhong
(74) *Attorney, Agent, or Firm* — Dentons US LLP; David Lanzotti, Esq.

(57) ABSTRACT

The disclosure provides DNA molecules and constructs, as well as their nucleotide sequences, useful for modulating gene expression in plants. The disclosure also provides nucleic acid sequences from *Arabidopsis thaliana* comprising novel regulatory elements identified from the AtHB17 gene. The disclosure also provides transgenic plants, plant cells, plant parts, and seeds comprising the DNA molecules operably linked to heterologous transcribable polynucleotides are also provided, as are methods of their use.

22 Claims, 17 Drawing Sheets
Specification includes a Sequence Listing.

(56) References Cited

FOREIGN PATENT DOCUMENTS

| WO | WO 2008/015263 | 2/2008 |
|---|---|---|
| WO | WO 2009/049373 | 4/2009 |
| WO | WO 2011/025840 | 3/2011 |
| WO | WO 2011/088065 | 4/2011 |
| WO | WO 2013/012775 | 1/2013 |
| WO | PCT/US14/58594 | 10/2014 |

OTHER PUBLICATIONS

Olsen et al., "NAC transcription factors: structurally distinct, functionally diverse," *Trends in Plant Science* 10(2):79-87, 2005.

Zhang et al., "Overexpression analysis of plant transcription factors," *Current Opinion in Plant Biology* 6:430-440, 2003.

U.S. Appl. No. 15/028,381, filed Apr. 8, 2016, Griffith et al.

GenBank Accession No. GE573225.1, dated Nov. 3, 2008.

U.S. Appl. No. 09/713,994, filed Nov. 16, 2000, Keddie et al.

Aso et al., "Characterization of Homeodomain-Leucine Zipper Genes in the Fern Ceratopteris richardii and the Evolution of the Homeodomain-Leucine Zipper Gene Family in Vascular Plants"; *Mol. Biol. Evol.* 16(4):544-552; 1999.

Barker et al., "Nucleotide sequence of the T-DNA region from the Agrobacterium tumefaciens octopine Ti plasmid pTi15955," *Plant Molecular Biology* 2:335-350, 1983.

Bevan et al., "Structure and transcription of the nopaline synthase gene region of T-DNA," *Nucleic Acids Research* 11(2):369-385,1983.

Bou-Torrent et al., "ATBH4 and HAT3, two class II HD-Zip transcription factors, control leaf development in *Arabidopsis*," *Plant Signal Behavior* 7(11):1382-1387, 2012.

Cao et al., "The *Arabidopsis* NPR1 Gene That Controls Systemic Acquired Resistance Encodes a Novel Protein Containing Ankyrin Repeats," *Cell* 88:57-63; Jan. 1997.

Clarke et al., "A colony bank containing synthetic Col El hybrid plasmids representative of the entire *E. coli* genome," *Cell* 9:91-99, 1976.

Collins, et al., "Molecular Characterization of the Maize Rp1-D Rust Resistance Haplotype and Its Mutants," *The Plant Cell*, 11:1365-1376, Jul. 1999.

Depicker et al, "Nopaline synthase: transcript mapping and DNA sequence," Journal of *Molecular and Applied Genetics* 1(6):561-573, 1982.

Dubose et al., "Use of microarray hybrid capture and next-generation sequencing to identify the anatomy of a transgene," *Nucleic Acids Research* 41:e70-e70, 2013.

Eddy, Profile Hidden Markov Models, *Bioinformatics Rev.*, 14(9):755-763, 1998.

Fling et al., "Nucleotide sequence of the transposon Tn7 gene encoding an aminoglycoside-modifying enzyme, 3"(9)-O-nucleotidyltransferase," *Nucleic Acids Research* 13(19):7095-7106, 1985.

Fraley et al., "Expression of bacterial genes in plant cells," *PNAS USA* 80:4803-4807, 1983.

Giza et al, "A self-inducing runaway-replication plasmid expression system utilizing the Rop protein," *Gene* 78:73-84, 1989.

Guo et al., "Protein tolerance to random amino acid change," *PNAS*, 101:9205-9210, 2004.

Hermann, "The shikimate pathway as an entry to aromatic secondary metabolism," *Plant Physiol* 107:7-12, 1995.

International Search Report and Written Opinion regarding International Application No. PCT/US2014/058585, dated Feb. 4, 2015.

Kay et al., "Duplication of CaMV 35S promoter sequences creates a strong enhancer for plant genes," *Science* 236(4806):1299-1302, 1987.

Keskin et al., "A new, structurally nonredundant, diverse data set of protein-protein interfaces and its implications", *Protein Science*,13:1043-1055, 2004.

Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet* 210(3):437-442, 1987.

Kovalic et al., "The use of next generation sequencing and junction sequence analysis bioinformatics to achieve molecular characterization of crops improved through modern biotechnology," *Plant Genome J* 5:149-163 , 2012.

Lall et al. "Quantitative Trait Loci Associated With Adventitious Shoot Formation in Tissue Culture and the Program of Shoot Development in *Arabidopsis*," *Genetics*, 167(4):1883-1892, 2004.

Lamppa et al., "Structure and developmental regulation of a wheat gene encoding the major chlorophyll a/b-binding polypeptide," *Mol Cell Biol* 5:1370-1378, 1985.

Larkin et al., "Roles of the GLABROUS1 and Transparent Testa GLABRA Genes in *Arabidopsis* Trichome Development," *The Plant Cell* 6:1065-1076; 1994.

Lazar et al., "Transforming Growth Factor a: Mutation of Aspartic Acid 47 and Leucine 48 Results in Different Biological Activities," *Mol. Cell Biol.* 1247-1252. 1988.

Lin et al., "Sequence and analysis of chromosome 2 of the plant *Arabidopsis thaliana*," *Nature*; 402:761-768, 1999.

Liu et al., "Two Transcription Factors, DREB1 and DREB2, with an EREBP/AP2 DNA binding domain separate two cellular signal transduction pathways in drought- and low-temperature-responsive gene expressing respectively, in *Arabidopsis*." *The Plant Cell*. Aug 10(8);1391-406; 1998.

McElroy et al., "Construction of expression vectors based on the rice actin 1 (Act1) 5' region for use in monocot transformation," *Mol Gen Genet* 231:150-160, 1991.

McElroy et al., "Isolation of an efficient actin promoter for use in rice transformation," *Plant Cell* 2:163-171, 1990.

McElwain et al, "A wheat cDNA clone which is homologous to the 17 kd heat-chock protein gene family of soybean," *Nucleic Acids Res* 17(4):1764-1764, 1989.

Meijer et al., "HD-Zip proteins of families I and II from rice interactions and functional properties"; *Molecular and General Genetics* ; 263:12-21; 2000.

NCBI Protein Sequence Accession No. Q8S9N6, Natl Lib of Medicine, NIH, Bethesda, MD, submitted Feb. 19, 2014.

Newman et al.,"Genes galore: a summary of methods for accessing results from large-scale partial sequencing of anonymous *Arabidopsis* cDNA clones," *Plant Physiology* 106:1241-1255; 1994.

Ngo et al., "The Protein Folding Problem and Tertiary Structure Prediction," Chapter 14, K. Merz, Jr., and S. Le Grand (eds.) 492-495, 1994.

Nishimura et al., "Over-Expression of Tobacco knotted 1-Type Class1 Homeobox Genes Alters Various Leaf Morphology," *Plant Cell Physiology*, 41(5):583-590, 2000.

Odell et al., "Identification of DNA sequences required for activity of the cauliflower mosaic virus 35S promoter," *Nature* 313:810-812, 1985.

Padgette et al., "New weed control opportunities: development of soybeans with Roundup Ready TM gene," In: Herbicide Resistant Crops, Padgette et al. (Eds.), CRC Press Inc., pp. 53-84, London, UK, 1996.

Riechmann et al., "*Arabidopsis* transcription factors: genome-wide comparative analysis among eukaryotes," *Science*; 290:2105-2110; 2000.

Rice et al., "Expression of a Truncated ATHB17 Protein in Maize Increases Ear Weight at Silking," *PLOS One* 9(4):e94238, 2014.

Ruberti et al., "A novel class of plant proteins containing a homeodomain with a closely linked leucine zipper motif," *EMBO J.* Jul:10(7); 1789-91; 1991.

Sakakibara et al., "Isolation of Homeodomain-Leucine Zipper Genes from the Moss Physcomitrella patens and the Evolution of Homeodomain-Leucine Zipper-Genes in Land Plants," *Mol. Biol. Evol.*, 18(4):491-502, 2001.

Salomon et al., "Capture of genomic and T-DNA sequences during double-strand break repair in somatic plant cells," *EMBO Journal* 17:6086-6095, 1998.

Schena et al., "The HAT4 gene of *Arabidopsis* encodes a developmental regulator," *Genes and Dev.*, 7(3):367-379,1993.

(56) References Cited

OTHER PUBLICATIONS

Schena et al., "Structure of homeobox-leucine zipper genes suggests a model for the evolution of gene families"; Proc. Natl. Acad. Sci. USA; 91:8393-8397; 1994.
Stalker et al., "Nucleotide Sequence of the Region of the Origin of Replication of the Broad Host Range Plasmid RK2," *Mol. Gen. Genet.* 181:8-12, 1981.
Thornton, et al. "From structure to function: Approaches and limitations," *Nature Structural Biology*, pp. 991-994, 2000.
Überlacker et al., "Ectopic Expression of the Maize Homeobox Genes ZmHox1a or ZmHox1b Causes Pleiotropic Alterations in the Vegetative and Floral Development of Transgenic Tobacco," *The Plant Cell*, 8:349-362,1996.
Vieira et al, "Production of single-stranded plasmid DNA," *Methods in Enzymology* 153:3-11, 1987.
Wells, "Additivity of mutational effects in proteins," *Biochemistry*; 29:8509-8517, 1990.
Whisstock, et al., "Prediction of protein function form protein sequence and structure," *Q. Rev. Biophys*. 36:307-340, 2003.
Zambryski et al., "Tumor induction by *Agrobacterium tumefaciens*: Analysis of the boundaries of T-DNA," *Journal of Molecular and Applied Genetics* 1:361-370, 1982.
Zhao et al., "Systematic analysis of sequences and expression patterns of grought-responsive members of the HD-Zip gene family in maize," *PLoS One* 6(12):e28488, 2011.
GenBank Accession No. H76651, dated Jan. 5, 1998.
GenBank Database Accession No. AF145727, dated Mar. 17, 2000.
GenBank Database Accession No. EU966190, dated Dec. 10, 2008.
GenBank Database Accession No. NM_001050228, dated Feb. 14, 2008.
GenPept Database Accession No. ACG38308, dated Dec. 10, 2008.
GenPept Database Accession No. EAY75147, dated Dec. 17, 2008.
GenPept Database Accession No. NP_001043693, dated Feb. 14, 2008.
USPTO: Image File Wrapper for U.S. Appl. No. 11/311,920 downloaded Jul. 16, 2015.
U.S. Appl. No. 14/507,734, filed Oct. 6, 2014, Adams et al.
U.S. Appl. No. 14/511,107, filed Oct. 9, 2014, Chomet et al.
U.S. Appl. No. 61/888,980, Oct. 9, 2013, Griffith et al.
GenBank Accession No. NM_126204, dated Jun. 5, 2013.
GenBank Accession No. AJ431181, dated Apr. 22, 2008.
GenBank Accession No. AC005560, dated Mar. 11, 2002.
GenBank Accession No. NP_178252, dated Jun. 5, 2013.
GenBank Accession No. AAC67320, dated Mar. 11, 2002.
Ariel et al., "The true story of the HD-Zip family," *Trends in Plant Science* 12(9):419-426, 2007.
Ciarbelli et al., "The *Arabidopsis* homeodomain-leucine zipper II gene family: diversity and redundancy," Plant Mol Biol 68:465-478, 2008.
Harris et al., "Modulation of plant growth by HD-Zip class I and II transcription factors in response to environmental stimuli," New Phytol 190:823-837, 2011.
Hymus et al., "Application of HB17, an *Arabidopsis* class II homeodomain-leucine zipper transcription factor, to regulate chloroplast number and photosynthetic capacity," *Journal of Experimental Botany* 64(14):4479-4490, 2013.
Ikeda et al., "A novel group of transcriptional repressors in *Arabidopsis*," Plant Cell Physiol 50(5):970-975, 2009.
Park et al., "ATHB17 is a positive regulator of abscisic acid response during early seedling growth," Mol Cells 35:125-133, 2013.

Turchi et al., "*Arabidopsis* HD-Zip II transcription factors control apical embryo development and meristem function," Development 140:2118-2129, 2013.
USPTO: Final Office Action regarding U.S. Appl. No. 14/511,107, dated Jan. 23, 2017.
European Supplementary Search Report regarding European Application No. 14852873.0, dated Feb. 14, 2017.
European Supplementary Search Report regarding European Application No. 14851966.3, dated Mar. 2, 2017.
Rice et al., "Expression of *Arabidopsis thaliana* HB17 Gene in Corn Leads to Improved Sink Potential," *In Vitro Cellular Developmental Biology—Animal* 49:S22, 2013. (Abstract).
Office Action regarding Chinese Application No. 201480055624.1, dated Mar. 9, 2017.
Zeng et al., "Genetic Engineering Technology," *China Light Industry Press* pp. 67-74, 2010.
USPTO: Interview Summary regarding U.S. Appl. No. 14/511,107, dated Apr. 12, 2017.
Steindler et al., "Shade avoidance responses are mediated by the ATHB-2 HD-Zip protein, a negative regulator of gene expression," *Development* 126:4235-4245, 1999.
Ohgishi et al., "Negative autoregulation of the *Arabidopsis* homeobox gene ATHB-2," *The Plant Journal* 25(4):389-398, 2001.
Qin et al., "Progress in HD-Zip Transcription Factors of Plants," *Chinese Journal of Cell Biology* 31(4):514-520, 2009.
Response to Final Office Action regarding U.S. Appl. No. 14/511,107, dated May 22, 2017.
USPTO: Advisory Action regarding U.S. Appl. No. 14/511,107, dated Jun. 12, 2017.
Hill et al., "Functional Analysis of Conserved Histidines in ADP-Glucose Pyrophosphorylase from *Excherichia coli*," *Biochem. Biophys. Res. Commun.* 244(2):573-577, 1998.
Hallauer, *Principles of Cultivar Development*, vol. 2, Walter Fehr ed., "Maize," pp. 249-294, 1987.
Hulbert et al., "Structure and Evolution of the rp1 Complex Conferring Rust Resistance in Maize," *Annual Review of Phytopathology* 35:293-310, 1997.
USPTO: Non-Final Office Action regarding U.S. Appl. No. 14/511,107, dated Aug. 27, 2018.
Response to Non-Final Office Action regarding U.S. Appl. No. 14/511,107, dated May 7, 2018.
USPTO: Non-Final Office Action regarding U.S. Appl. No. 14/511,107, dated Jan. 17, 2018.
Nishimura et al., "Over-Expression of Tobacco knotted1-Type Class1 Homeobox Genes Alters Various Leaf Morphology," *Plant Cell Physiol*. 41(5):583-590, 2000.
Ruzza et al., ATB17_ARATH, 2002.
Sentoku et al., "Overexpression of Rice OSH Genes Induces Ectopic Shoots on Leaf Sheaths of Transgenic Rice Plants," *Developmental Biology* 220:358-364, 2000.
Silverstone et al., "Gibberellins and the Green Revolution," *Trends in Plant Science* 5(1):1-2, 2000.
Ueki et al., "Functional transient genetic transformation of *Arabidopsis* leaves by biolistic bombardment," *Nature Protocols* 4(1):71-77, 2009.
U.S. Appl. No. 16/160,841, filed Oct. 15, 2018, Adams et al.
Response to Non-Final Office Action regarding U.S. Appl. No. 14/511,107, dated Feb. 26, 2019.
USPTO: Non-Final Office Action regarding U.S. Appl. No. 15/028,381, dated Apr. 12, 2019.
USPTO: Notice of Allowance and Fee(s) Due regarding U.S. Appl. No. 14/511,107, dated Jun. 11, 2019.

\* cited by examiner

SEQUENCE LISTING

<160> NUMBER OF SEQ ID NOS: 6

<210> SEQ ID NO 1
<211> LENGTH: 65
<212> TYPE: DNA
<213> ORGANISM: Arabidopsis thaliana

<400> SEQUENCE: 1
gcttctcttc atcccctctc tccgatgaag gaagtggcgg aggaagagac cagctaaggc    60
tagac                                                                65

<210> SEQ ID NO 2
<211> LENGTH: 489
<212> TYPE: DNA
<213> ORGANISM: Arabidopsis thaliana

<400> SEQUENCE: 2
atgaatcggt taccgtcgtc tgaagacgga gacgatgaag aattcagtca cgatgatggc    60
tctgctcctc cgcgaaagaa actccgtcta accagagaac agtcacgtct tcttgaagat   120
agtttcagac agaatcatac ccttaatccc aacaaaagg aagtacttgc caagcatttg    180
atgctacggc caagacaaat tgaagtttgg tttcaaaacc gtagagcaag gagcaaattg   240
aagcaaaccg agatggaatg cgagtatctc aaaaggtggt ttggttcatt aacgaagaa    300 aaccacaggc tccatagaga agtagaagag cttagagcca taaggttgg cccaacaacg    360 gtgaactctg cctcgagcct tactatgtgt cctcgctgcg agcgagttac ccctgccgcg   420
agcccttcga gggcggtggt gccggttccg gctaagaaaa cgtttccgcc gcaagagcgt   480
gatcgttag                                                           489

<210> SEQ ID NO 3
<211> LENGTH: 162
<212> TYPE: PRT
<213> ORGANISM: Arabidopsis thaliana

<400> SEQUENCE: 3

Met Asn Arg Leu Pro Ser Ser Glu Asp Gly Asp Asp Glu Glu Phe Ser
1               5                   10                  15

His Asp Asp Gly Ser Ala Pro Pro Arg Lys Lys Leu Arg Leu Thr Arg
            20                  25                  30

Glu Gln Ser Arg Leu Leu Glu Asp Ser Phe Arg Gln Asn His Thr Leu
        35                  40                  45

Asn Pro Lys Gln Lys Glu Val Leu Ala Lys His Leu Met Leu Arg Pro
    50                  55                  60

Arg Gln Ile Glu Val Trp Phe Gln Asn Arg Arg Ala Arg Ser Lys Leu
65                  70                  75                  80

Lys Gln Thr Glu Met Glu Cys Glu Tyr Leu Lys Arg Trp Phe Gly Ser
                85                  90                  95

Leu Thr Glu Glu Asn His Arg Leu His Arg Glu Val Glu Glu Leu Arg
            100                 105                 110

Ala Ile Lys Val Gly Pro Thr Thr Val Asn Ser Ala Ser Ser Leu Thr
        115                 120                 125

Met Cys Pro Arg Cys Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

```
<210> SEQ ID NO 4
<211> LENGTH: 65
<212> TYPE: DNA
<213> ORGANISM: Arabidopsis thaliana

<400> SEQUENCE: 4
gcttctcttc atccctctc tccgacgaag gaagtggcgg aggaagagac cagctaaggc    60
tagac                                                               65

<210> SEQ ID NO 5
<211> LENGTH: 275
<212> TYPE: PRT
<213> ORGANISM: Arabidopsis thaliana

<400> SEQUENCE: 5

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 6
<211> LENGTH: 828
<212> TYPE: DNA
```

```
<213> ORGANISM: Arabidopsis thaliana

<400> SEQUENCE: 6
atgataaaac tactatttac gtacatatgc acatacacat ataaactata tgctctatat      60
catatggatt acgcatgcgt gtgtatgtat aaatataaag gcatcgtcac gcttcaagtt     120
tgtctctttt atattaaact gagagttttc ctctcaaact ttaccttttc ttcttcgatc     180
ctagctctta agaaccctaa taattcattg atcaaaataa tggcgatttt gccggaaaac     240
tcttcaaact tggatcttac tatctccgtt ccaggcttct cttcatcccc tctctccgat     300
gaaggaagtg gcggaggaag agaccagcta aggctagaca tgaatcggtt accgtcgtct     360
gaagacggag acgatgaaga attcagtcac gatgatggct ctgctcctcc gcgaaagaaa     420
ctccgtctaa ccagagaaca gtcacgtctt cttgaagata gtttcagaca gaatcatacc     480
cttaatccca aacaaaagga agtacttgcc aagcatttga tgctacggcc aagacaaatt     540
gaagtttggt ttcaaaaccg tagagcaagg agcaaattga agcaaaccga gatggaatgc     600
gagtatctca aaaggtggtt tggttcatta acggaagaaa accacaggct ccatagagaa     660
gtagaagagc ttagagccat aaaggttggc ccaacaacgg tgaactctgc ctcgagcctt     720
actatgtgtc ctcgctgcga gcgagttacc cctgccgcga gcccttcgag ggcggtggtg     780
ccggttccgg ctaagaaaac gtttccgccg caagagcgtg atcgttga                  828
```

PLANT REGULATORY ELEMENTS AND USES THEREOF

CROSS REFERENCE TO RELATED APPLICATIONS

This application claims the benefit of U.S. Provisional Application No. 61/888,972 filed Oct. 9, 2013, herein incorporated by reference in its entirety

INCORPORATION OF SEQUENCE LISTING

The sequence listing that is contained in the file named "MONS341US_ST25.txt", which is 10 KB (as measured in Microsoft Windows®) and was created on Oct. 9, 2014, is filed herewith by electronic submission and is incorporated by reference herein.

FIELD

The disclosure relates to the field of plant molecular biology. More specifically, the disclosure relates to novel plant regulatory elements and methods of using the same.

BACKGROUND

Regulatory elements are genetic elements that regulate gene activity by modulating the transcription of an operably linked transcribable polynucleotide molecule. Such elements may include promoters, leaders, introns, and 3' untranslated regions and are useful in the field of plant molecular biology and plant genetic engineering.

Manipulation and control of gene expression in plants is vital to the success of plant genetic engineering. Newly introduced genetic elements are collectively referred to as transgenes. A typical transgene comprises, from 5'- to 3'-end, a regulatory sequence, a full or partial coding region in sense or antisense orientation, and often a terminator region. Many variables affect the final expression pattern of the transgene, including, for example, the insertion site of the transgene in the plant genome, the strength and specificity of the regulatory sequence, preferred codon usage in the plant genome, the strength and specificity of the regulatory sequence, preferred codon usage in the targeted plant species, and the presence of cryptic splice sites or cryptic poly A sites.

SUMMARY

In one aspect, the invention provides a recombinant polynucleotide comprising a genetic regulatory element operably linked 5' to a leader regulatory element comprising SEQ ID NO:1 or SEQ ID NO:4 operably linked 5' to a transcribable polynucleotide, wherein the recombinant polynucleotide lacks polynucleotides 1-293 of SEQ ID NO:6. In one embodiment, the leader regulatory element comprises SEQ ID NO: 1. In another embodiment, the leader regulatory element comprises SEQ ID NO:4. In another embodiment, the transcribable polynucleotide comprises a sequence encoding the polypeptide of SEQ ID NO:3.

In another aspect, the invention provides a transgenic plant cell comprising a recombinant polynucleotide according to the invention. In one embodiment, the transgenic plant cell is a monocotyledonous plant cell. In another embodiment, the transgenic plant cell is a dicotyledonous plant cell.

In yet another aspect, the invention provides a transgenic plant, or part thereof, comprising the recombinant polynucleotide of the invention. In another aspect, the invention provides a transgenic seed comprising the recombinant polynucleotide.

In still yet another aspect, the invention provides a method of producing a commodity product comprising obtaining the transgenic plant or part thereof and producing the commodity product therefrom. In one embodiment, the commodity product is grain, starch, seed, meal, flour, biomass, or seed oil.

In still yet another aspect, the invention provides a method of increasing the yield of a plant comprising expressing in leaf tissue of the plant a polypeptide comprising SEQ ID NO:3 at a level of from about 0.001 ppm to about 0.5 ppm, wherein the plant lacks at least a first off-type. In one embodiment, the polypeptide is expressed at a level of from about 0.001 ppm to about 0.1 ppm. In another embodiment, the yield of grain from said plant is increased over the yield of an otherwise isogenic plant not expressing said polypeptide of SEQ ID NO:3.

In still yet another aspect, the invention provides a method for increasing at least one agronomic trait selected from the group consisting of ear biomass, ear size, ear diameter, ear length, kernel size, kernel number per plant, kernel weight or increased grain yield as measured at R6 comprising expressing in V6 leaf tissue of a corn plant a polypeptide comprising SEQ ID NO:3 at a level of from about 0.001 ppm to about 0.1 ppm. In one embodiment, at least one agronomic trait is increased over that of an otherwise isogenic plant not expressing said polypeptide of SEQ ID NO:3.

In still yet another aspect, the present invention provides a method of obtaining corn seed comprising a transformation event that confers increased ear biomass, ear size, ear diameter, ear length, kernel size, kernel number per plant, kernel weight or increased yield at R6 comprising: (a) obtaining a population of corn plants each comprising a transformation event that encodes the polypeptide of SEQ ID NO:3; (b) identifying at least a first corn plant that expresses the polypeptide of SEQ ID NO:3 in V6 leaf tissue in an amount of from about 0.001 ppm to about 0.1 ppm; and (c) collecting seed from said first corn plant. In one embodiment, at least a first member of the population of plants comprises the recombinant polynucleotide.

In still yet another aspect, the invention provides a method for producing transgenic seeds that, when grown, produce plants with increased yield resulting from expression of a recombinant polynucleotide of the invention, wherein said method comprises: (a) obtaining a population of transgenic plants comprising a transgene that comprises the recombinant polynucleotide of the invention; and (b) collecting seed or a regenerable propagule from said plant. In one embodiment, the method further comprises selecting from said population at least a first plant that exhibits increased yield as compared to the yield of an otherwise isogenic control plant. In another embodiment, the method further comprises confirming that said transgene is stably integrated in said plant that exhibits increased yield. In another embodiment, the method further comprises confirming that said plant expresses the polypeptide sequence of SEQ ID NO:3 at a level of less than about 0.1 ppm in V6 leaf tissue. In another embodiment, the transgenic plants are corn plants.

In still yet another aspect, the invention provides a method of producing corn grain with increased yield comprising: (a) planting seeds comprising the recombinant polynucleotide of claim 1; (b) cultivating plants and said seeds; and (c) harvesting grain from said plants.

BRIEF DESCRIPTION OF THE SEQUENCES

SEQ ID NO:1—Genetic regulatory element in nucleotides 275-339 of *Arabidopsis thaliana* ATHB17 coding region (herein referred to as ATHB17-nt275-339)

SEQ ID NO:2—Coding sequence of *Arabidopsis thaliana* ATHB17 truncation variant ATHB17Δ113

SEQ ID NO:3—Amino acid sequence of *Arabidopsis thaliana* ATHB17 truncation variant ATHB17Δ113

SEQ ID NO:4—Variant of ATHB17-nt275-339

SEQ ID NO:5—Amino acid sequence of *Arabidopsis thaliana* ATHB17 full length protein SEQ ID NO:6—Coding sequence of *Arabidopsis thaliana* ATHB17 full length polynucleotide

BRIEF DESCRIPTION OF THE FIGURES

FIG. 8A: ATHB17 protein and RNA levels in V6 leaf; FIG. 8B: single kernel weight The Y axis represents % change compared to control. The light grey bar represents 0.1<p≤0.2; FIG. 8C: broad acre yield (bushels per acre delta). Error bar represent 90% of confidence interval. Bars with different shade of grey represent different testers.

FIG. 9A: ATHB17 protein and RNA levels in V6 leaf; FIG. 9B: single kernel weight. The Y axis represents % change compared to control. The light grey bar represents 0.1<p≤0.2; FIG. 9C: broad acre yield (bushels per acre delta). Error bar represent 90% of confidence interval. Bars with different shade of grey represent different testers.

DETAILED DESCRIPTION

Figure 1:
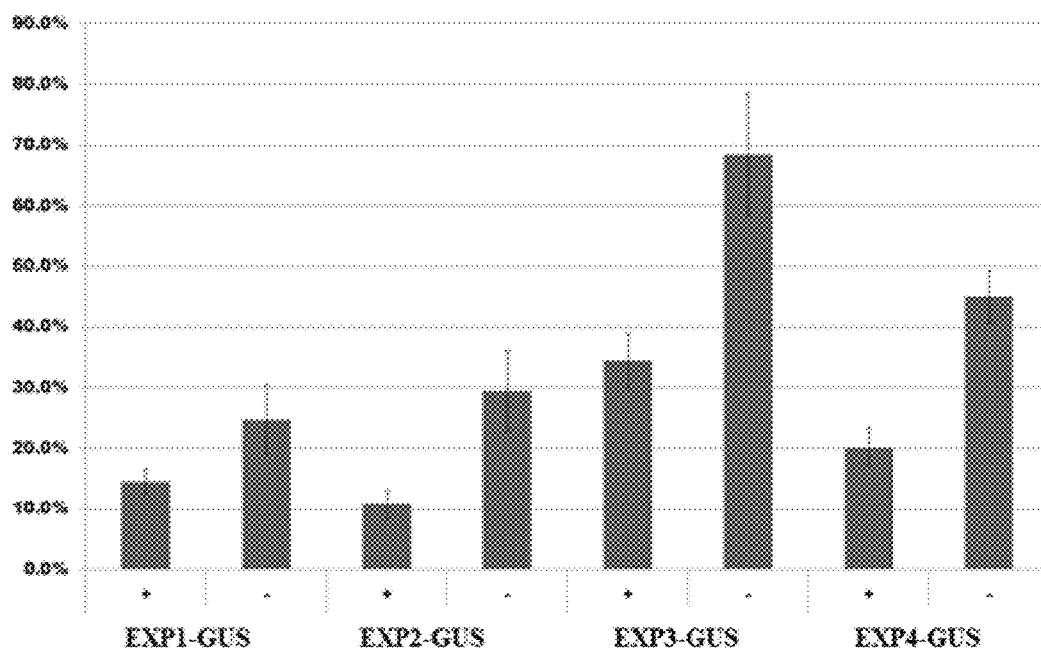
FIG. 1: A graphical representation of the average percent GUS/RLuc relative to GUS Control in corn leaf protoplasts.

The following detailed description is provided to better define the present disclosure and to guide those of ordinary skill in the art in the practice of the present disclosure. Unless otherwise noted, terms are to be understood according to conventional usage by those of ordinary skill in the relevant art.

The disclosure disclosed herein provides polynucleotide molecules having beneficial gene regulatory activity. The polynucleotide molecules with gene regulatory activity were identified from the ATHB17 gene (a.k.a. AtG1543) from *Arabidopsis thaliana*, which encodes a transcription factor. The polynucleotide molecules of the present invention are not present in *A. thaliana* as discreet genetic regulatory molecules. The design, construction, and use of these polynucleotide molecules are one aspect of this disclosure. The polynucleotide sequences of these polynucleotide molecules were surprisingly found to be capable of beneficially affecting the expression of operably linked transcribable polynucleotide molecules in plant cells and can regulate gene expression in transgenic plants. In this manner, the polynucleotide sequences can result in transgenic plants with improved phenotypes. In some instances, off-types may be associated with higher levels of expression associated with expression of some transgenes that do not comprise the regulatory sequences described herein. The present disclosure therefore provides methods of using such sequences, as well as methods of producing constructs and transgenic plants comprising such sequences. The disclosure also includes compositions, transformed host cells comprising the genetic regulatory element, and methods for preparing and using the same.

In one embodiment, the disclosure provides a genetic regulatory element originally isolated from an alternatively spliced variant of the ATHB17 gene. The genetic regulatory element of the invention appears to act as a leader sequence for transcription of genes when operably linked thereto. The alternatively spliced variant has a 274 nt truncation at the N-terminus of the protein coding region, which is equivalent to the first 91 amino acids of the full length ATHB17 protein. As the next in-frame translation start site is at amino acid position 114 of the full length protein, the translation of a truncated ATHB17 polypeptide lacking the first 113 amino acids is produced, referred to herein as ATHB17Δ113. The transcript produced from the alternatively spliced variant includes a 65 nucleotide leader (5' UTR) sequence (interchangeably called ATHB17-nt275-339 genetic regulatory element or ATHB17-nt275-339) before the first in-frame start codon of the truncated ATHB17Δ113 polypeptide. As described, the leader surprisingly reduces transcription and translation of operably linked downstream transcribable polynucleotides. The reduced protein expression levels can confer improved phenotypes in transgenic plants, while higher protein expression levels can lead to off-types. The reduction of transcription and translation caused by the novel leader regulatory element is not promoter-specific or gene-specific and results in suppression of transcription and translation in both monocot and dicot plant cells. Transgenic corn plants carrying the novel regulatory element for expression of the ATHB17Δ113 polypeptide, for example, showed increased yield together without the off-types that were sometimes observed with expression not using the regulatory element.

In one embodiment, the disclosure thus provides recombinant polynucleotides comprising a leader regulatory element from an alternatively spliced variant of the ATHB17 gene. In some embodiments, the regulatory element comprises the nucleotide sequence of SEQ ID NO:1 or SEQ ID NO:4. The design, construction, and use of these polynucleotide molecules are provided by the disclosure. These polynucleotide molecules are, for instance, capable of use in the design of expression constructs for any given coding or non-coding transcribable polynucleotide, thereby providing a desired level of expression. The disclosure also provides compositions, transformed host cells, and seeds comprising such polynucleotides, and methods for preparing and using the same.

In one embodiment, the disclosure provides recombinant polynucleotides comprising a leader regulatory element from an alternatively spliced variant of the ATHB17 gene, which when present 5' to the ATHB17Δ113 sequence, results in reduced transcription and translation of ATHB17Δ113. In another embodiment, the expression of ATHB17Δ113 produces a polypeptide of SEQ ID NO:3. In further embodiments, the regulatory element comprises the nucleotide sequence of SEQ ID NO:1 or SEQ ID NO:4. In another embodiment, presence of the regulatory element comprising the nucleotide sequence of SEQ ID NO:1 or SEQ ID NO:4 5' to the ATHB17Δ113 sequence results in reduced expression of ATHB17Δ113. In yet another embodiment, presence of the regulatory element in a plant comprising the nucleotide sequence of SEQ ID NO:1 or SEQ ID NO:4 5' to the ATHB17Δ113 sequence results in reduced level of polypeptide encoded by ATHB17Δ113 as compared to plant carrying said ATHB17Δ113 sequence but lacking said regulatory element of SEQ ID NO:1 or SEQ ID NO:4. In some embodiments, the reduction of the level of said polypeptide may be as much as 20 fold. In further embodiments, the reduction of the level of said polypeptide may be as much as 19, 18, 17, 16, 15, 14, 13, 12, 11, 10, 9, 8, 7, 6, 5, 4, 3, or 2 fold.

The following definitions and methods are provided to better define the present disclosure and to guide those of ordinary skill in the art in the practice of the present disclosure. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, the term "recombinant" refers to a technique of combining two or more macromolecules (polynucleotides or polypeptides) or the combined molecule resulting therefrom. For example, transgenes and constructs are recombinant polynucleotides.

Any number of methods well known to those skilled in the art can be used to isolate and manipulate a DNA molecule, or fragment thereof, disclosed in the present disclosure. For example, PCR (polymerase chain reaction) technology can be used to amplify a particular starting DNA molecule and/or to produce variants of the original molecule. DNA molecules, or fragments thereof, can also be obtained by other techniques such as by directly synthesizing the fragment by chemical means, as is commonly practiced by using an automated oligonucleotide synthesizer.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a leader regulatory element is operably linked to a transcribable polynucleotide molecule if the leader regulates transcription of the transcribable polynucleotide molecule of interest in a cell.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NO:1 or SEQ ID NO:4.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the disclosure provides a DNA molecule comprising a sequence that when optimally aligned to a reference sequence, provided herein as SEQ ID NO:1 and SEQ ID NO:4, has at least about 85 percent identity, at least about 90 percent identity, at least about 95 percent identity, at least about 96 percent identity, at least about 97 percent identity, at least about 98 percent identity, or at least about 99 percent identity to the reference sequence. In some embodiments, such sequences may be defined as having gene-regulatory activity.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric leader" refers to a leader produced through such manipulation of DNA molecules. A chimeric leader regulatory element may combine two or more DNA fragments; an example would be the fusion of a leader to an enhancer element. Thus, the design, construction, and use of chimeric leaders according to the methods disclosed herein for modulating the expression of operably linked transcribable polynucleotide molecules are encompassed by the present disclosure.

As used herein, the term "variant" refers to a second DNA molecule that is in composition similar, but not identical to, a first DNA molecule, and yet the second DNA molecule still maintains the general functionality, i.e. the same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present disclosure, a polynucleotide sequence provided as SEQ ID NO:1 or SEQ ID NO:4 may be used to create variants that are in composition similar, but not identical to, the polynucleotide sequence of the original regulatory element, while still maintaining the general functionality, i.e. the same or similar expression pattern, of the original regulatory element. Production of such variants of the present disclosure is well within the ordinary skill of the art in light of the disclosure and is encompassed within the scope of the present disclosure.

Chimeric regulatory element "variants" comprise the same constituent elements as a reference sequence, but the constituent elements comprising the chimeric regulatory element may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting chimeric regulatory element "variant" can be comprised of the same, or variants of the same, constituent elements of the reference sequence but differ in the sequence or sequences that comprise the linking sequence or sequences that allow the constituent parts to be operatively linked. In the present disclosure, a polynucleotide sequence provided as SEQ ID NO:1 or SEQ ID NO:4 provides a reference sequence wherein the constituent elements that comprise the reference sequence may be joined by methods known in the art and may comprise substitutions, deletions, and/or insertions of one or more nucleotides or mutations that naturally occur in bacterial and plant cell transformation.

Genetic Regulatory Elements

The term "genetic regulatory element" refers to a DNA molecule having gene regulatory activity, i.e. one that has the ability to affect the transcription and/or translation of an operably linked transcribable polynucleotide molecule. The term "gene regulatory activity" thus refers to the ability to affect the expression of an operably linked transcribable polynucleotide molecule by affecting the transcription and/or translation of that operably linked transcribable polynucleotide molecule. As used herein, a transcriptional regulatory expression element group or "EXP" sequence may be comprised of expression elements, such as enhancers, promoters, leaders, and introns, operably linked. Thus, a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small fragment comprising the second intron/exon splice junction so as to provide for proper intron/exon processing to facilitate transcription and proper processing of the resulting transcript. Leaders and introns may alter transcription of an operably linked transcribable polynucleotide molecule, as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may alter the translation of the messenger RNA molecule.

Regulatory elements such as promoters, leaders, introns, and transcription termination regions (or 3' UTRs) are DNA molecules that have gene regulatory activity and play an integral part in the overall expression of genes in living cells. Isolated regulatory elements, such as promoters and leaders that function in plants, are therefore useful for modifying plant phenotypes through the methods of genetic engineering.

Regulatory elements may be characterized by their expression pattern effects (qualitatively and/or quantitatively), e.g. positive or negative effects and/or constitutive or other effects, such as by their temporal, spatial, developmental, tissue, environmental, physiological, pathological, cell cycle, and/or chemically responsive expression pattern, and any combination thereof, as well as by quantitative or qualitative indications. A leader is useful as a regulatory element for modulating the expression of an operably linked transcribable polynucleotide molecule.

As used herein, the term "gene expression" means transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" means translation of a transcribed RNA molecule into a protein molecule. Protein expression may be characterized by its temporal, spatial, developmental, or morphological qualities, as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is, a promoter produced through the fusion of two or more heterologous DNA molecules. Promoter molecules and any variants or derivatives thereof as described herein, are further defined as comprising promoter activity, i.e., are capable of acting as a promoter in a host cell, such as in a transgenic plant cell. A fragment may be defined as exhibiting promoter activity possessed by the starting promoter molecule from which it is derived, or a fragment may comprise a "minimal promoter" that provides a basal level of transcription and is comprised of a TATA box or equivalent sequence for recognition and binding of the RNA polymerase II complex for initiation of transcription.

As used herein, the term "leader" or "leader regulatory element" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. The genetic regulatory element that act as leader molecules of the present disclosure may thus be operably linked to their native promoter or may be operably linked to a heterologous promoter. Such genetic regulatory elements that act as leaders useful in practicing the present disclosure include SEQ ID NO:1 and SEQ ID NO:4 or fragments or variants thereof. In some embodiments, such sequences may be defined as being capable of acting as a leader in a host cell, including, for example, a transgenic plant cell. In one embodiment, such sequences are denoted as comprising leader activity.

The leader sequences (5' UTR) presented as SEQ ID NO:1 and SEQ ID NO:4 may be comprised of regulatory elements, or may adopt secondary structures that can have an effect on transcription or/and translation of a transgene. The leader sequences presented as SEQ ID NO:1 and SEQ ID NO:4 can be used in accordance with the disclosure to make chimeric regulatory elements that affect transcription or/and translation of a transgene. In addition, the leader sequences presented as SEQ ID NO:1 and SEQ ID NO:4 can be used to make chimeric leader sequences that affect transcription or/and translation of a transgene.

In one embodiment, fragments are provided of a leader regulatory element sequence disclosed herein. Leader fragments may comprise regulatory activity, as described above, and may be useful alone or in combination with other leaders and leader fragments, such as in constructing chimeric leaders. In some embodiments, fragments of a leader are provided comprising at least about 10, 15, 20, 25, 30, 35, 40, 45, 50, 55, 56, 57, 58, 59, 60, 61, 62, 63, 64, and 65 contiguous nucleotides, of a polynucleotide molecule having regulatory activity disclosed herein.

In accordance with the disclosure, a leader regulatory element (5' UTR) or leader fragment may be analyzed for the presence of various elements. Identification of such leader elements may be used by one of skill in the art to design variants of the leader having a similar effect on the expression pattern of operatively linked downstream transcribable polynucleotides as compared to the original leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that affect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347).

In plants, the inclusion of some introns in gene constructs leads to modified mRNA and protein accumulation relative to constructs lacking the intron. Introns known to stimulate expression in plants have been identified in maize genes [e.g. tubA1, Adh1, Sh1, Ubi1 (Jeon et al., *Plant Physiol.* 123:1005-1014, 2000; Callis et al., *Genes Dev.* 1:1183-1200, 1987; Vasil et al., *Plant Physiol.* 91:1575-1579, 1989; Christiansen et al., *Plant Mol. Biol.* 18:675-689, 1992)] and in rice genes [e.g. salt, tpi (McElroy et al., *Plant Cell* 2:163-171, 1990; Xu et al., *Plant Physiol.* 106:459-467, 1994)]. Similarly, introns from dicotyledonous plant genes like those from *petunia* (e.g. rbcS), potato (e.g. st-ls1) and from *Arabidopsis thaliana* (e.g. ubq3 and pat1) have been found to modify gene expression rates (Dean et al., *Plant Cell* 1:201-208, 1989; Leon et al., Plant Physiol. 95:968-972, 1991; Norris et al., *Plant Mol Biol* 21:895-906, 1993; Rose and Last, *Plant J.* 11:455-464, 1997). It has been shown that deletions or mutations within the splice sites of an intron reduce gene expression, indicating that splicing might be needed for intron-mediated enhancement (IME) (Mascarenhas et al., *Plant Mol Biol.* 15:913-920, 1990; Clancy and Hannah, *Plant Physiol.* 130:918-929, 2002). However, that splicing per se is not required for a certain IME in dicotyledonous plants has been shown by point mutations within the splice sites of the pat1 gene from *A. thaliana* (Rose and Beliakoff, *Plant Physiol.* 122:535-542, 2000).

Compositions derived from the introns can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+ leader and coding sequence. When modifying intron/exon boundary sequences, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified in this manner. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

The introduction of a transgene into a plant host does not always result in optimal expression of the incoming gene. Furthermore, if dealing with complex traits, it is sometimes necessary to modulate several genes with spatially or temporally different expression patterns. Introns can provide such modulation. However, multiple uses of the same intron in one plant have shown to exhibit disadvantages. In those cases, it is necessary to have a collection of basic control elements for the construction of appropriate recombinant DNA elements. In one embodiment, leader regulatory elements can be one such basic control element. In another embodiment, the leader regulatory element may provide for a way to modulate expression of a downstream transcribable element by reducing the expression level. In another embodiment, said leader regulatory element may modulate expression of a downstream transcribable element by reducing the expression to very low levels.

As used herein, the term "enhancer" or "enhancer element" refers to a cis-acting transcriptional regulatory element, a.k.a. cis-element, which confers an aspect of the overall expression pattern, but is usually insufficient alone to drive transcription of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that affect the transcription of operably linked genes. Many promoter enhancer elements are believed to bind DNA-binding proteins and/or affect DNA topology, producing local conformations that selectively allow or restrict access of RNA polymerase to the DNA template, or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain.

Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequent manipulation. Thus, the design, construction, and use of enhancer elements according to the methods disclosed herein for modulating the expression of operably-linked transcribable polynucleotide molecules are encompassed by the present disclosure.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley et al., *Proc. Natl. Acad. Sci. USA,* 80: 4803-4807, 1983); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445, 1999; Proudfoot, *Nature* 322:562-565, 1986; Kim et al., *Biotechnology Progress* 19:1620-1622, 2003; Yonaha and Proudfoot, *EMBO J.* 19:3770-3777, 2000; Cramer et al., *FEBS Letters* 498:179-182, 2001; Kuerstem and Goodwin, *Nature Reviews Genetics* 4:626-637, 2003). Effective termination of RNA transcription is required to prevent unwanted transcription of trait-unrelated (downstream) sequences, which may interfere with trait performance.

In plants, clearly defined polyadenylation signal sequences are not known. Hasegawa et al. (*Plant J.* 33:1063-1072, 2003) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334, 2001). Appropriate control of transcription termination can prevent read-through into sequences (e.g. other expression cassettes) localized downstream and can further allow efficient recycling of RNA polymerase to improve gene expression. Efficient termination of transcription (release of RNA Polymerase II from the DNA) is a pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, and thus it is difficult to detect transcriptional termination sites by conventional methods. Moreover, prediction of functional and efficient 3' UTRs by bioinformatics methods is difficult in that there are no conserved sequences that would allow easy prediction of an effective 3' UTR.

The 3' UTR is involved in the regulation of transcript cleavage and polyadenylation, controls alternative polyadenylation, nuclear export, and in many cases, is critical for determining transcript stability, level of translation, and mRNA targeting. Transcript degradation may either start from poly(A)-shortening or from deadenylation-independent endonucleolytic cleavage. Protein binding to the cis-acting regions in the 3' UTR influences both processes, thus determining mRNA stability. Protein binding to cis-acting elements in the 3' UTR can either be sequence-specific, or promoted by structural elements (stem-loops) formed in the mRNA (Grzybowska et al., *Biochemical and Biophysical Research Communications* 288:291-295, 2001). The termination of transcription and stabilization of specific transcripts by 3' UTR proteins can depend on protein-RNA interactions near the site of the regulatory event at the 3' terminus. Translational control mechanisms have been identified where the regulatory mRNA-binding protein does not bind near the mRNA region that is responsible for regulation. An example of such a mechanism is that of the 3' UTR-binding proteins that regulate the initiation of translation in the distant 5' region of the mRNA. For example, dipeptidyl carboxypeptidase (Dcp1, the protein that removes the m$^7$GpppNcap) binds to the 5' terminus of the transcript and also interacts with the 3 '-interacting poly(A) binding protein (PABP). This interaction brings the 5' and 3' end of the mRNA together forming a 'closed loop' or circular structure. Biochemical evidence for such a mechanism is provided by the discovery in yeast that the poly(A)-bound PABP also interacts with the translation initiation factor eIF4G, which in turn interacts with the cap-binding protein eIF4E, thereby effectively circularizing the mRNA via end-to-end complex formation (Mazumder et al., *Trends in Biochem Sci,* 28:91-98, 2003).

From a practical standpoint, it is typically beneficial that a 3' UTR used in a transgene cassette possesses the following characteristics: (1) The 3' UTR should be able to efficiently and effectively terminate transcription of the transgene and prevent read-through of the transcript into any neighboring DNA sequence, which can be comprised of another transgene cassette as in the case of multiple cassettes residing in one T-DNA, or the neighboring chromosomal DNA into which the T-DNA has inserted; (2) The 3' UTR should not cause a reduction in the transcriptional activity imparted by the promoter, leader (5' UTR) and introns that are used to drive expression of the transgene, unless reduction of expression is a desired characteristic for certain plant tissues to more finely tune expression of the transgene.

In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from tissues isolated from selected plant species using methods known to those skilled in the art from flower tissue, seed, leaf, and root, among other tissue types. The resulting cDNAs may be sequenced using various sequencing methods known in the art. The resulting ESTs are assembled into clusters using bioinformatics software, such as cic_ref_assemble_complete version 2.01.37139 (CLC bio USA, Cambridge, Mass. 02142). Transcript abundance of each cluster can be determined by counting the number of cDNA reads for each cluster. The cDNA sequence is used to design primers, which may then be used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance, either by direct counts or normalized counts of observed sequence reads for each tissue library, can be used to infer properties about patterns of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the leader, the introns, or the 3' UTR. Empirical testing of 3' UTRs identified by the properties of expression within specific organs, tissues, or cell types can result in the identification of 3' UTRs that enhance expression in those specific organs, tissues, or cell types. These identified properties allow one to "fine tune" the expression of certain transgenes to provide more optimal expression of the transgenes.

The introduction of a transgene into a plant host does not always result in optimal expression of the incoming gene. As shown herein, high-level expression may result in off-types in transgenic plants. By use of a regulatory element of the disclosure, an appropriate level of expression may be maintained to achieve beneficial phenotypes.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

The constructs of the present disclosure may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the present disclosure.

Methods are known in the art for assembling and introducing constructs into a cell in such a manner that the transcribable polynucleotide molecule is transcribed into a functional mRNA molecule that may be translated and expressed as a protein product. For the practice of the present disclosure, conventional compositions and methods for preparing and using constructs and host cells are well known to one skilled in the art, see, for example, *Molecular Cloning: A Laboratory Manual*, $3^{rd}$ edition Volumes 1, 2, and 3, J. Sambrook, D. W. Russell, and N. Irwin, Cold Spring Harbor Laboratory Press, 2000. Methods for making recombinant vectors suited to plant transformation include, without limitation, those described in U.S. Pat. Nos. 4,971, 908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, 1988; and Glick, et al., *Methods in Plant Molecular Biology and Biotechnology*, CRC Press, Boca Raton, Fla., 1993). Typical vectors useful for expression of nucleic acids in higher plants are well known in the art and include vectors derived from the tumor-inducing (Ti) plasmid of *Agrobacterium tumefaciens* (Rogers et al., *Methods in Enzymology* 153: 253-277, 1987). Other recombinant vectors useful for plant transformation, including the pCaMVCN transfer control vector, have also been described in the scientific literature (see, for example, Fromm et al., *Proc. Natl. Acad. Sci. USA* 82: 5824-5828, 1985).

Various regulatory elements may be included in a construct including any of those provided herein. Any such regulatory elements may be provided in combination with other regulatory elements. Such combinations can be designed or modified to produce desirable regulatory features. In one embodiment, constructs of the present disclosure comprise at least one regulatory element operably linked to a transcribable polynucleotide molecule operably linked to a 3' UTR. A DNA construct may comprise an intron, and the intron may or may not be heterologous with respect to the transcribable polynucleotide molecule sequence.

Constructs and vectors may also include a transit peptide coding sequence that expresses a linked peptide useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633, 435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into an RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

In one embodiment, a genetic regulatory element or leader regulatory element (5' UTR) of the present disclosure may be operably linked to a transcribable polynucleotide molecule that may or may not be heterologous with respect to the leader molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. Thus, in one embodiment of the disclosure the leader can be heterologous with respect to an operably linked transcribable polynucleotide molecule if such a combination is not normally found in nature, i.e. that transcribable polynucleotide molecule is not naturally occurring operably linked in combination with that leader molecule.

In another embodiment, a genetic regulatory element or leader regulatory element (5' UTR) of the present disclosure may be operably linked to a transcribable polynucleotide molecule that is native with respect to the leader molecule. In some embodiments, the leader regulatory element may be linked to an ATHB17Δ113 coding sequence.

The transcribable polynucleotide molecule may generally be any DNA molecule for which expression of an RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In some embodiments, this may be accomplished through the use of inhibitory RNA. In one embodiment, this may be accomplished by using a transcribable polynucleotide molecule that is oriented in the antisense direction. As the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the disclosure provides a genetic regulatory element or leader regulatory element of the present disclosure, such as those provided as SEQ ID NO:1 or SEQ ID NO:4, operably linked to a transcribable polynucleotide molecule so as to decrease transcription of the transcribable polynucleotide molecule at a desired level or in a desired pattern when the construct is integrated in the genome of a plant cell. In one embodiment, the transcribable polynucleotide molecule comprises a protein-coding region of a gene, and the leader regulatory element affects the transcription of an RNA molecule that is translated and expressed as a protein product. In another embodiment, the transcribable polynucleotide molecule comprises an antisense region of a gene, and the leader regulatory element affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent, such as an antisense or RNAi molecule targeting a particular gene for suppression. The product of a gene of agronomic interest may act within the plant in order to cause an effect upon the plant physiology or metabolism, or may act as a pesticidal agent in the diet of a pest that feeds on the plant.

In one embodiment of the disclosure, a leader regulatory element of the present disclosure is incorporated into a construct such that the leader is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oil production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. In another embodiment, a beneficial agronomic trait is increased ear biomass, increased ear size, increased ear diameter, increased ear length, increased kernel size, increased kernel number per plant, increased kernel weight and increased yield at physiological maturity (R6 in corn). As used herein, the term "ear" may refer to the ear alone, the ear and the associated husk, or the ear, the associated husk and the associated shank tissues.

Examples of genes of agronomic interest known in the art include those for herbicide resistance (U.S. Pat. Nos. 6,803, 501; 6,448,476; 6,248,876; 6,225,114; 6,107,549; 5,866, 775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653, 280; 6,573,361; 6,506,962; 6,316,407; 6,215,048; 5,516, 671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; and 6,476,295), modified oil production (U.S. Pat. Nos. 6,444, 876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589, 767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

A gene of agronomic interest can affect the above mentioned plant characteristic or phenotype by encoding a molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The molecule could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed molecule, such as an RNA molecule, that affects an agronomically important phenotype or morphology change of interest may be useful for the practice of the present disclosure.

Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US 2007/0124836) and compositions isolated from nematode pests (U.S. Patent Publication No. US 2007/ 0250947). Plant pests include, but are not limited to arthropod pests, nematode pests, and fungal or microbial pests.

Exemplary transcribable polynucleotide molecules for incorporation into constructs of the present disclosure include, for example, DNA molecules or genes from a species other than the target species or genes that originate with or are present in the same species, but are incorporated into recipient cells by genetic engineering methods rather than classical reproduction or breeding techniques. The type of polynucleotide molecule may include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present disclosure include, but are not limited to transcribable polynucleotide molecules encoding ß-glucuronidase (GUS, described in U.S. Pat. No. 5,599,670), green fluorescent protein and variants thereof (GFP, described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and to which the method of the present disclosure can be applied, include, but are not limited to: amino-methylphosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and may include, but are not limited to, a transcribable polynucleotide molecule encoding 5-enolpyruvylshikimate-3-phosphate synthase (EPSPS, for glyphosate tolerance, described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX, described in U.S. Pat. No. 5,463,175; GAT, described in U.S. Patent publication No. US 2003/0083480); a transcribable polynucleotide molecule encoding dicamba monooxygenase (DMO, U.S. Patent publication No. US 2003/0135879) for dicamba tolerance; a transcribable polynucleotide molecule encoding bromoxynil nitrilase (Bxn for Bromoxynil tolerance, described in U.S. Pat. No. 4,810,648); a transcribable polynucleotide molecule encoding phytoene desaturase (crtI) described in Misawa, et al. (*Plant Journal* 4:833-840, 1993; and *Plant Journal* 6:481-489, 1994) for norflurazon tolerance; a transcribable polynucleotide molecule encoding acetohydroxyacid synthase (AHAS, aka ALS) described by Sathasiivan, et al. (*Nucl. Acids Res.* 18:2188-2193, 1990) for tolerance to sulfonylurea herbicides; and the bar gene described by DeBlock, et al. (*EMBO Journal* 6:2513-2519, 1987) for glufosinate and bialaphos tolerance. The leader regulatory element molecules of the present disclosure can modulate expression of operably linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes that can be detected catalytically. Selectable secreted marker proteins fall into a number of classes, including small, diffusible proteins that are detectable, (e.g. by ELISA), small active enzymes that are detectable in extracellular solution (e.g, α-amylase, β-lactamase, phosphinothricin transferase), or proteins that are inserted or trapped in the cell wall (such as proteins which include a leader peptide sequence such as that found in the expression unit of extension or tobacco pathogenesis related proteins also known as tobacco PR-S). Other possible selectable marker genes will be apparent to those of skill in the art and are encompassed by the present disclosure.

Cell Transformation

The disclosure is also directed to a method of producing transformed cells and plants that comprise a leader regulatory element operably linked to a transcribable polynucleotide molecule.

The term "transformation" refers to the introduction of nucleic acid into a recipient host. As used herein, the term "host" refers to bacteria, fungi, or plants, including any cells, tissue, organs, or progeny of the bacteria, fungi, or plants. Plant tissues and cells of interest include protoplasts, meristems, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to bacteria, fungi, or plants containing one or more heterologous polynucleic acid molecules.

There are many methods for introducing polynucleic acid molecules into plant cells. Such methods generally comprise the steps of selecting a suitable host cell, transforming the host cell with a recombinant vector, and obtaining a transformed host cell. Suitable methods may include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, and the like (reviewed in Potrykus, et al., *Ann. Rev. Plant Physiol. Plant Mol. Biol.* 42: 205, 1991).

Technology for introduction of a DNA molecule into cells is well known to those of skill in the art. Methods and materials for transforming plant cells by introducing a plant DNA construct into a plant genome in the practice of this disclosure can include any of the well-known and demonstrated methods. Any transformation method may be utilized to transform a host cell with one or more leaders and/or constructs of the present disclosure. Host cells may be any cell or organism, such as a plant cell, algal cell, algae, fungal cell, fungi, bacterial cell, or insect cell. Examples of hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98, 1960; Simmonds, *Principles of crop improvement*, Longman, Inc., NY, 369-399, 1979; Sneep and Hendriksen, Plant breeding perspectives, Wageningen (ed), Center for Agricultural Publishing and Documentation, 1979; Fehr, *Soybeans: Improvement, Production and Uses*, 2nd Edition, Monograph, 16:249, 1987; Fehr, *Principles of variety development, Theory and Technique*, (Vol. 1) and *Crop Species Soybean* (Vol 2), Iowa State Univ., Macmillan Pub. Co., NY, 360-376, 1987. Conversely, pollen from non-transgenic plants may be used to pollinate the regenerated transgenic plants.

The transformed plants may be analyzed for the presence of the genes of interest and the expression level and/or profile conferred by the regulatory elements of the present disclosure. Those of skill in the art are aware of the numerous methods available for the analysis of transformed plants. For example, methods for plant analysis include, but are not limited to Southern blots or Northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this disclosure can be harvested from fertile transgenic plants and used to grow progeny generations of transformed plants of this disclosure, including hybrid plant lines comprising a construct of this disclosure and expressing a gene of agronomic interest.

The present disclosure also provides for parts of the plants of the present disclosure. Plant parts, without limitation, include leaves, stems, roots, tubers, seeds, endosperm, ovule, and pollen. The disclosure also includes and provides transformed plant cells which comprise a nucleic acid molecule of the present disclosure.

The present disclosure also provides for propagules of the plants of the present disclosure. As used herein a "propagule" includes all products of meiosis and mitosis, including but not limited to, plant, seed and part of a plant able to propagate a new plant. Propagules also include cells, pollen, ovules, flowers, embryos, leaves, roots, stems, shoots, meristems, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

The transgenic plant may pass along the transgenic polynucleotide molecule to its progeny. Progeny may include any regenerable plant part or seed comprising the transgene derived from an ancestor plant. The transgenic plant may be homozygous for the transformed polynucleotide molecule and transmit that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as Western blots, Northern blots, immuno-precipitation, and ELISA.

Having now generally described the invention, the same will be more readily understood through reference to the following examples which are provided by way of illustration, and are not intended to be limiting of the present disclosure, unless specified. It should be appreciated by those of skill in the art that the techniques disclosed in the following examples represent techniques discovered by the inventors to function well in the practice of the disclosure. However, those of skill in the art should, in light of the present disclosure, appreciate that many changes can be made in the embodiments that are disclosed and still obtain a like or similar result without departing from the spirit and scope of the disclosure, therefore all matter set forth or shown in the accompanying drawings is to be interpreted as illustrative and not in a limiting sense.

EXAMPLES

Example 1

Cloning of the ATHB17-nt275-339 Genetic Regulatory Element

During the course of experimentation, it was observed that a fragment of the *Arabidopsis* ATHB17 gene sequence possessed gene regulatory activity. This 65 nucleotide fragment, herein referred to as ATHB17-nt275-339 (SEQ ID NO:1) was isolated and cloned into plasmid vectors in which various 5' transcriptional regulatory elements were used to drive expression of the ß-glucuronidase (GUS) transgene in both corn and soybean leaf protoplasts to assess the effect on gene expression exerted by ATHB17-nt275-339. Plasmid vectors were also constructed to assess the effect on gene expression using a luciferase gene derived from firefly (*Photinus pyralis*).

Plasmid vectors were constructed using methods known in the art. A first set of plasmids were designed to assay the effect on gene expression imparted by the regulatory DNA element, ATHB17-nt275-339 (SEQ ID NO:1) using 4 different transcriptional regulatory expression element group (EXP) sequences or "EXPs". Each plasmid contained a transgene cassette comprised of an EXP sequence operably linked 5' to a GUS coding sequence which was in turn operably linked to a 3' UTR. Two plasmids each were constructed using the same EXP sequence; one plasmid comprising the regulatory DNA element, ATHB17-nt275-339 (SEQ ID NO:1) operably linked 3' to the EXP sequence and operably linked 5' to the GUS coding sequence (designated as EXPn-GUS+, where n=1, or 2 or 3 or 4 as described in Table 1 or in other examples; also shown in the horizontal axis of FIGS. 2 and 3 as "+"). The other plasmid that possessed the same EXP sequence lacked the regulatory DNA element ATHB17-nt275-339 and instead was comprised of the same EXP sequence operably linked 5' to the GUS coding sequence (designated as EXPn-GUS-, where n=1, or 2 or 3 or 4 as described in Table 1 and in other examples; also shown in the horizontal axis of FIGS. 2 and 3 as "−"). Table 1 below shows the constructed plasmids and elements comprising their respective transgene cassettes as well as the associated EXPs and their corresponding operably linked regulatory elements. These plasmids were used to transform corn and soybean protoplasts as is described in Examples 2 and 3, respectively.

In addition, two control plasmids (GUS Control and GFP Control) were constructed using known methods. These two plasmids are also presented in Table 1. The plasmid GUS Control was used in the experiments presented in Examples 2 and 3 as a comparator for GUS expression of the other plasmids. The plasmid GFP Control was used in the experiments presented in Examples 2 and 3 as a negative control for GUS expression. The GFP Control expression cassette comprised of the same genetic regulatory elements as in the GUS Control expression cassette. Both GUS Control and GFP Control were used as negative controls for luciferase expression in Examples 4 and 5 below.

TABLE 1

Plasmid vectors and transgene cassette genetic elements

| Plasmid | Annotation | Description |
| --- | --- | --- |
| EXP1-GUS+ | CaMV.35S duplicated enhancer | Enhancer |
| | Os.Act1 | Promoter |
| | Ta.Lhcb | Leader |
| | ATHB17-nt275-339 | Genetic Regulatory Element (SEQ ID NO: 1) in nucleotides 275-339 of ATHB17 coding region |
| | Ec.uidA | GUS Coding Sequence |
| | Ta.Hsp17 | 3' UTR |
| EXP1-GUS− | CaMV.35S duplicated enhancer | Enhancer |
| | Os.Act1 | Promoter |
| | Ta.Lhcb | Leader |
| | Ec.uidA | GUS Coding Sequence |
| | Ta.Hsp17 | 3' UTR |
| EXP2-GUS+ | CUCme.Ubq10 | Promoter |
| | CUCme.Ubq10 | Leader |

TABLE 1-continued

Plasmid vectors and transgene cassette genetic elements

| Plasmid | Annotation | Description |
|---|---|---|
| | CUCme.Ubq10 | Intron |
| | ATHB17-nt275-339 | Genetic Regulatory Element (SEQ ID NO: 1) in nucleotides 275-339 of ATHB17 coding region |
| | Ec.uidA | GUS Coding Sequence |
| | Ta.Hsp17 | 3' UTR |
| EXP2-GUS− | CUCme.Ubq10 | Promoter |
| | CUCme.Ubq10 | Leader |
| | CUCme.Ubq10 | Intron |
| | Ec.uidA | GUS Coding Sequence |
| | Ta.Hsp17 | 3' UTR |
| EXP3-GUS+ | SETit.Ubql | Promoter |
| | SETit.Ubql | Leader |
| | SETit.Ubql | Intron |
| | ATHB17-nt275-339 | Genetic regulatory element (SEQ ID NO: 1) in nucleotides 275-339 of ATHB17 coding region |
| | Ec.uidA | GUS Coding Sequence |
| | Ta.Hsp17 | 3' UTR |
| EXP3-GUS− | SETit.Ubql | Promoter |
| | SETit.Ubql | Leader |
| | SETit.Ubql | Intron |
| | Ec.uidA | GUS Coding Sequence |
| | Ta.Hsp17 | 3' UTR |
| EXP4-GUS+ | DaMV.FLT | Enhancer |
| | DaMV.FLT | Promoter |
| | DaMV.FLT | Leader |
| | ATHB17-nt275-339 | Genetic regulatory element (SEQ ID NO:1) in nucleotides 275-339 of ATHB17 coding region |
| | Ec.uidA | GUS Coding Sequence |
| | Ta.Hsp17 | 3' UTR |
| EXP4-GUS− | DaMV.FLT | Enhancer |
| | DaMV.FLT | Promoter |
| | DaMV.FLT | Leader |
| | Ec.uidA | GUS Coding Sequence |
| | Ta.Hsp17 | 3' UTR |
| GUS Control | CaMV.35S-enh | Promoter |
| | CaMV.35S | Leader |
| | Zm.DnaK | Intron |
| | Ec.uidA | GUS Coding Sequence |
| | AGRtu.nos | 3' UTR |
| GFP Control | CaMV.35S-enh | Promoter |
| | CaMV.35S | Leader |
| | Zm.DnaK | Intron |
| | Av.GFP_S65T.nno+St.LS | GFP Coding Sequence |
| | AGRtu.nos | 3' UTR |

Table 2 below shows plasmids that were constructed to assay the effect of the regulatory DNA element, ATHB17-nt275-339 on expression of a coding sequence for firefly luciferase that are presented in Examples 4 and 5.

TABLE 2

Plasmid vectors and transgene cassette genetic elements link in 5' to 3' direction used in the experiments presented in Examples 4 and 5

| Plasmid | Annotation | Description |
|---|---|---|
| EXP5-FLuc+ | CaMV.35S duplicated enhancer | Enhancer |
| | Os.Actl | Promoter |
| | Ta.Lhcbl | Leader |
| | ATHB17-nt275-339 | Genetic regulatory element (SEQ ID NO: 1) in nucleotides 275-339 of ATHB17 coding region |
| | PHOpy.FLuc | Firefly Luciferase Coding Sequence |
| | Ta.Hsp17 | 3' UTR |

TABLE 2-continued

Plasmid vectors and transgene cassette genetic elements link in 5' to 3' direction used in the experiments presented in Examples 4 and 5

| Plasmid | Annotation | Description |
|---|---|---|
| EXP5-FLuc− | CaMV.35S duplicated enhancer | Enhancer |
| | Os.Actl | Promoter |
| | Ta.Lhcbl | Leader |
| | PHOpy.FLuc | Firefly Luciferase Coding Sequence |
| | Ta.Hsp17 | 3' UTR |

The EXP sequences used to drive expression of GUS and Luciferase were comprised of various 5' transcriptional regulatory elements. For example, as shown in Tables 1 and 2, EXP1 is comprised of the enhancer element, CaMV.35S, operably linked 5' to the promoter element, Os.Act1, which is operably linked 5' to the leader element, Ta.Lhcb1. Likewise, as shown in Table 1, the EXP2 is comprised of the promoter element, CUCme.Ubq10, operably linked 5' to the leader element, CUCme.Ubq10, which is operably linked to the intron element, CUCme.Ubq10. Other EXP's are linked similarly, as outlined in Table 1 and 2.

Example 2

Analysis of the Effect of the ATHB17-Nt275-339 Genetic Regulatory Element on GUS Expression in Corn Leaf Protoplasts Corn leaf protoplasts were transformed with the constructs presented in Table 1 above and used to assay the effect of the ATHB17-nt275-339 genetic regulatory element on gene expression using the GUS coding sequence. Four pairs of plasmid vectors were constructed as described in Example 1 above, each plasmid pair comprising the same EXP sequence and 3' UTR. One plasmid of each pair had the ATHB17-nt275-339 genetic regulatory element operably linked 3' to the EXP sequence and operably linked 5' to the GUS coding sequence. The other plasmid of each plasmid pair contained a transgene cassette that was comprised of the same EXP sequence operably linked 5' to the GUS coding sequence but lacked the ATHB17-nt275-339 genetic regulatory element. Quantitative analysis of GUS expression was performed and the level of expression compared between the two plasmids of each plasmid pair. The quantitative expression levels were then analyzed with respect to a GUS expression control plasmid described below.

Two control plasmids, GUS Control and GFP Control were used. The plasmid GUS Control is comprised of CaMV.35S-enh+Zm.DnaK, driving GUS expression. This control plasmid was used as a positive control for GUS expression and the quantitative values derived from the plasmid pairs were provided as percent expression relative to expression of GUS Control. The control plasmid GFP Control was comprised of CaMV.35S+Os.Act1+Ta.Lhcb1, driving GFP expression. This control plasmid was used as a negative control for GUS and luciferase expression. A no DNA control was used to provide background values for GUS and luciferase.

The plasmid RLuc Control was also constructed using methods known in the art for use in co-transformation and normalization of data. Plasmid vector RLuc Control was comprised of a transgene cassette with CaMV.35S-enh-Lhcb1, operably linked 5' to a sea pansy (*Renilla reniformis*) luciferase coding sequence (Ren.hRenilla Lucife), operably linked 5' to a 3' UTR from the *Agrobacterium tumefaciens* nopaline synthase gene (AGRtu.nos).

Corn leaf protoplasts were transformed using a PEG-based transformation method, as is well known in the art. Protoplast cells were transformed with 0.3 μg/320,000 cells of RLuc Control plasmid DNA and 5.0 μg/320,000 cells of one of the plasmids presented in Table 1 of Example 1 and incubated overnight in total darkness. Measurements of both GUS and luciferase activities were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using four replicates of each transformation, each replicate sample utilizing 6000 cells. Background GUS and luciferase (RLuc) was determined from the no DNA control cells. The average GUS and RLuc background values from the 4 replicate samples was then subtracted from each of the GUS and RLuc measures made from cells transformed with the plasmids shown in Table 1 of Example 1. A GUS/RLuc ratio was calculated for each replicate sample using the background subtracted GUS and RLuc values. A percent GUS/RLuc value for GUS control was calculated for each of the 4 replicate samples by dividing each replicate sample GUS/RLuc ratio by the average of the 4 GUS Control GUS/RLuc ratios and multiplying by 100. Each replicate sample GUS/RLuc of plasmids, EXP1-GUS+, EXP1-GUS−, EXP2-GUS+, EXP2-GUS−, EXP3-GUS+, EXP3-GUS−, EXP4-GUS+ and EXP4-GUS− was then expressed as a percent of the corresponding replicate sample GUS/RLuc of GUS Control.

An average of the percent GUS/RLuc was determined for each plasmid sample. Table 3 below shows these calculated averages from the corn leaf protoplasts. FIG. 1 provides a graphical representation of the average percent GUS/RLuc relative to GUS Control in corn leaf protoplasts. In both Table 3 and FIG. 1, plasmid vectors comprising transgene cassettes wherein the ATHB17-nt275-339 genetic regulatory element is operably linked to the GUS coding sequence are indicated with a "+" character. Those plasmid vectors lacking the ATHB17-nt275-339 genetic regulatory element are indicated with a "−" character. "N/A" in Table 3 indicates "not applicable".

TABLE 3

Average percent GUS/RLuc from corn leaf protoplasts.

| Plasmid | SEQ ID NO: 1 | Relative Percent GUS/RLuc to control (GUS Control) | stdev |
| --- | --- | --- | --- |
| EXP1-GUS+ | + | 14.50% | 2.10% |
| EXP1-GUS− | − | 24.80% | 5.70% |
| EXP2-GUS+ | + | 10.80% | 2.40% |
| EXP2-GUS− | − | 29.50% | 6.70% |
| EXP3-GUS+ | + | 34.50% | 4.50% |
| EXP3-GUS− | − | 68.50% | 10.10% |
| EXP4-GUS+ | + | 20.30% | 3.10% |
| EXP4-GUS− | − | 45.00% | 4.30% |
| GUS Control | N/A | 100.00% | 35.40% |
| GFP Control | N/A | 0.00% | 0.00% |

As can be seen in Table 3 and FIG. 1, the expression of GUS was reduced when the regulatory element ATHB17-nt275-339 was operably linked 3' to 5' regulatory elements and operably linked 5' to the coding sequence (GUS). This attenuation of expression was consistent for all EXP's. For the plasmid pairs EXP2-GUS+/EXP2-GUS−, EXP3-GUS+/EXP3-GUS− and EXP4-GUS+/EXP4-GUS−, there was at least a two fold reduction in expression. For the plasmid pair EXP1-GUS+/EXP1-GUS− expression was reduced around 1.7 fold. The regulatory element ATHB17-nt275-339 (SEQ ID NO:1) acts as an attenuator of protein expression.

Example 3

Analysis of the Effect of the ATHB17-nt275-339 Genetic Regulatory Element on GUS Expression in Soybean Leaf Protoplasts Soybean leaf protoplasts were transformed with the constructs presented in Table 1, Example 1, and Example 2 above and used to assay the effect of the ATHB17-nt275-339 genetic regulatory element on gene expression using the GUS coding sequence. Soybean leaf protoplasts were transformed as described above and GUS and RLuc values were determined as described in Example 2.

Figure 2:
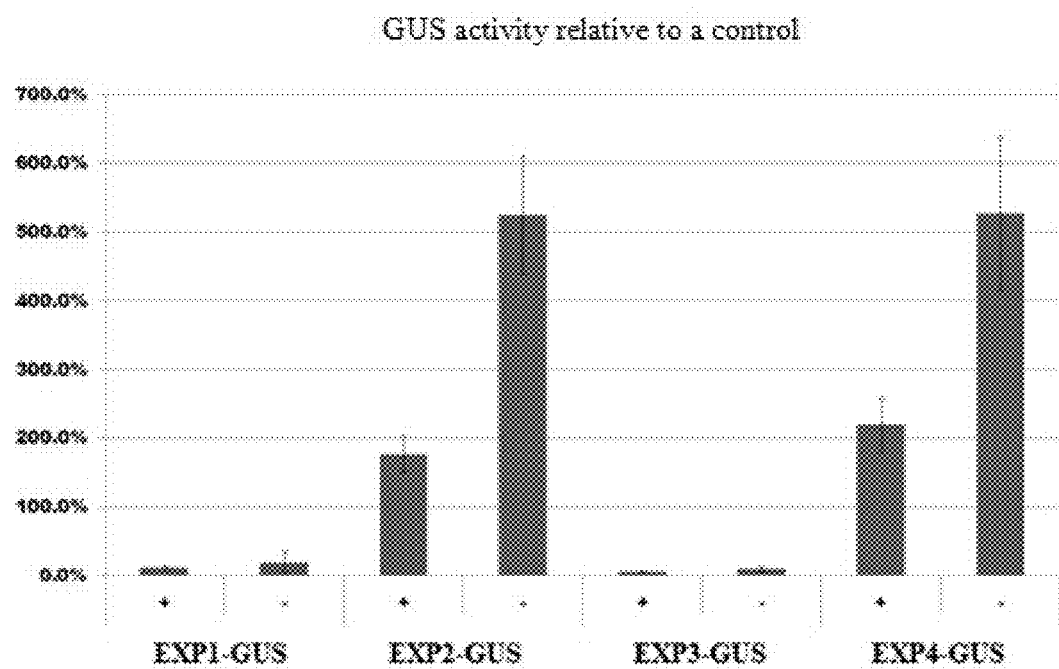
FIG. 2: A graphical representation of the average percent GUS/RLuc relative to GUS Control in soybean leaf protoplasts.

Table 4 below shows the calculated average of the percent GUS/RLuc determined for each plasmid sample (N/A=not applicable) in soybean leaf protoplasts. FIG. 2 provides a graphical representation of the average percent GUS/RLuc relative to GUS Control in soybean leaf protoplasts.

TABLE 4

Average percent GUS/RLuc from soybean leaf protoplasts

| Plasmid | SEQ ID NO: 1 | Relative GUS activities to control (GUS Control) | stdev |
| --- | --- | --- | --- |
| EXP1-GUS+ | + | 11.3% | 3.2% |
| EXP1-GUS− | − | 19.3% | 15.0% |
| EXP2-GUS+ | + | 176.3% | 26.1% |
| EXP2-GUS− | − | 524.5% | 85.3% |
| EXP3-GUS+ | + | 6.3% | 1.9% |
| EXP3-GUS− | − | 10.0% | 4.8% |
| EXP4-GUS+ | + | 219.0% | 40.9% |
| EXP4-GUS− | − | 527.3% | 111.5% |
| GUS Control | N/A | 100.0% | 23.0% |
| GFP Control | N/A | 1.0% | 2.0% |

As can be seen in Table 4 above and in FIG. 2, the expression of GUS was reduced when the regulatory element ATHB17-nt275-339 was operably linked 3' to 5' regulatory elements and operably linked 5' to the coding sequence (GUS). This attenuation of expression was consistent for all EXP's. The plasmid vectors EXP1-GUS+, EXP1-GUS−, EXP3-GUS+ and EXP3-GUS− contain transgene cassettes that comprise EXP's that express better in monocot cells than in dicot cells, but the overall trend of a reduction in expression caused by ATHB17-nt275-339 is still evident. There is a greater than two fold reduction observed between the plasmid pairs EXP2-GUS+/EXP2-GUS− as well as EXP4-GUS+/EXP4-GUS−. An attenuation of expression was also observed in the plasmid pairs EXP1-GUS+/EXP1-GUS− and EXP3-GUS+/EXP3-GUS−.

Example 4

Analysis of the Effect of the ATHB17-nt275-339 Genetic Regulatory Element on Luciferase Expression in Corn Leaf Protoplasts Corn leaf protoplasts were transformed with the constructs presented in Table 1 and Table 2 above and used to assay the effect of the ATHB17-nt275-339 genetic regulatory element on gene expression using the firefly (*Photinus pyralis*) luciferase coding sequence.

The plasmid pair shown in Table 2 or Example 1, EXP5-FLuc+ and EXP5-FLuc– comprised the same EXP (CaMV.35S-Os.Act1/Ta.Lhcb1), and 3' UTR (Ta.Hsp17). The transgene cassette of plasmid EXP5-FLuc+ comprises the ATHB17-nt275-339 regulatory element operably linked 3' to the EXP sequence and operably linked 5' to the firefly (*Photinus pyralis*) luciferase coding sequence (PHOpy.hF-Luc), while the transgene cassette of plasmid EXP5-FLuc– lacks the ATHB17-nt275-339 regulatory element. Corn leaf protoplasts were transformed with each of these plasmids along with the two control plasmids, GUS Control and GFP Control. The control plasmids were used in this experiment as negative controls for firefly luciferase activity (herein referred to as FLuc).

Corn leaf protoplasts were transformed using a PEG-based transformation method, as is well known in the art. Protoplasts were transformed with 0.3 µg/320,000 cells of RLuc Control (described in Example 2 above) plasmid DNA and 5.0 µg/320,000 cells of one of the plasmids presented in Table 2 of Example 1 and incubated overnight in total darkness. Measurements of both firefly and sea pansy luciferase were conducted by placing aliquots of a lysed preparation of cells transformed as above into small-well trays. Activity of both luciferase genes (FLuc and RLuc) were determined using a dual luciferase assay; the dual luciferase reporter assay system (Promega Corp., Madison, Wis.; see for example, Promega Notes Magazine, No: 57, 1996, p. 02). Sample measurements were made using four replicates of each transformation, each replicate sample utilizing 6000 cells. Background sea pansy luciferase (RLuc) was determined from a no DNA control. The average RLuc background values from the 4 replicate no DNA samples was then subtracted from each of the RLuc measures made from cells transformed with the plasmids shown in Table 2 of Example 1.

Figure 3:
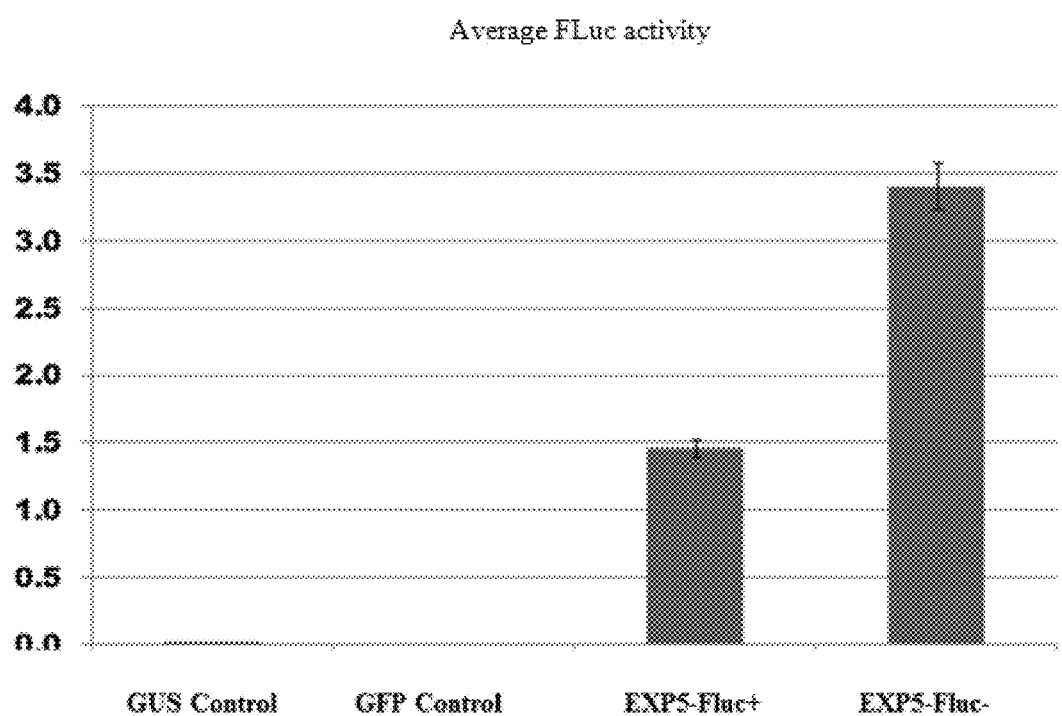
FIG. 3: A graphical representation of the average ratios of FLuc/RLuc in corn leaf protoplasts.

An average FLuc/RLuc was derived from each of the 4 samples for each plasmid transformation. Table 5 below shows the calculated FLuc/RLuc ratios. FIG. 3 shows a graphical representation of the average FLuc/RLuc ratios. In both Table 5 and FIG. 3, plasmid vectors comprising transgene cassette wherein the ATHB17-nt275-339 genetic regulatory element was operably linked to the firefly luciferase coding sequence are indicated with a "+" character. The plasmid vector lacking the ATHB17-nt275-339 genetic regulatory element is indicated with a "–" character.

TABLE 5

Average FLuc/RLuc of transformed corn leaf protoplasts

| Plasmid | Cassette | SEQ ID NO:1 | Average FLuc/RLuc | stdev |
|---|---|---|---|---|
| GUS Control | Control | N/A | 0 | 0 |
| GFP Control | | N/A | 0 | 0 |
| EXP5-FLuc+ | Luciferase | + | 1.46 | 0.07 |
| EXP5-FLuc– | | – | 3.41 | 0.17 |

As can be seen in Table 5 above and in FIG. 3, the ATHB17-nt275-339 genetic regulatory element attenuated expression of the firefly luciferase gene in a similar manner as the attenuation of expression of GUS demonstrated in Examples 2 and 3 above.

Example 5

Analysis of the Effect of the ATHB17-nt275-339 Genetic Regulatory Element on Luciferase Expression in Soybean Leaf Protoplasts Soybean leaf protoplasts were transformed with the constructs presented in Table 2 (Example 1) and Example 4 above and used to assay the effect of ATHB17-nt275-339 genetic regulatory element on gene expression using the firefly luciferase coding sequence. Soybean leaf protoplasts were transformed as described above and FLuc, RLuc and FLuc/RLuc values were determined and manipulated as described in Example 4.

Figure 4:
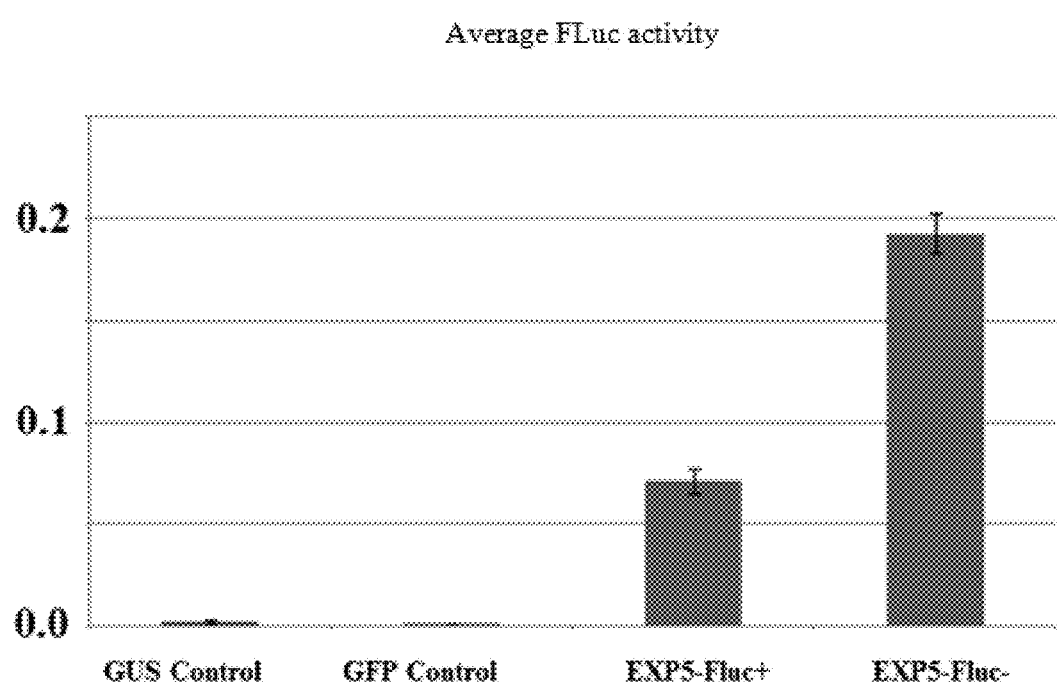
FIG. 4: A graphical representation of the average ratios of FLuc/RLuc in soybean leaf protoplasts.

Table 6 below shows the calculated FLuc/RLuc ratios. FIG. 4 shows a graphical representation of the average FLuc/RLuc ratios in soybean leaf protoplasts.

TABLE 6

FLuc, background subtracted RLuc and FLuc/RLuc of transformed soybean leaf protoplast

| Plasmid | Cassette | SEQ ID NO:1 | Average Fluc activities (normalized to Rluc) | stdev |
|---|---|---|---|---|
| GUS Control | Control | N/A | 0.00 | 0.00 |
| GFP Control | | N/A | 0.00 | 0.00 |
| EXP5-FLuc+ | Luciferase | + | 0.07 | 0.01 |
| EXP5-FLuc– | | – | 0.19 | 0.01 |

The transgene cassette EXP sequence of EXP5-FLuc+ and EXP5-FLuc– was designed to express well in monocots due to the use of the rice actin promoter in operable linkage to the enhancer and leader elements. Even though expression in both plasmids was lower in soybean protoplasts in comparison to expression in corn protoplasts, the attenuation of the firefly luciferase gene expression imparted by the ATHB17-nt275-339 regulatory element is still evident. In both corn and soybean leaf protoplast, expression of the firefly luciferase gene was reduced at least two fold when the ATHB17-nt275-339 genetic regulatory element was operably linked 3' to the EXP sequence and operably linked 5' to the coding sequence (firefly luciferase).

Example 6

Analysis of the Effect of the ATHB17-nt275-339 Genetic Regulatory Element on ATHB17Δ113 Expression in Corn Leaf Protoplasts Corn leaf protoplasts were transformed with the constructs presented in Table 7 above and used to assay the effect of the ATHB17-nt275-339 genetic regulatory element on gene expression using the ATHB17Δ113 coding sequence.

The plasmid pair shown in Table 7 below, EXP5-ATHB17Δ113+ and EXP5-ATHB17Δ113– comprised the same EXP (EXP-CaMV.35S/Os.Act1/Ta.Lhcb1) and 3' UTR (Ta.Hsp17). The transgene cassette of plasmid EXP5-ATHB17Δ113+ comprised the ATHB17-nt275-339 regulatory element operably linked 3' to the EXP sequence and operably linked 5' to the ATHB17Δ113 coding sequence (SEQ ID NO:2). The transgene cassette of plasmid EXP5-ATHB17Δ113– lacked the ATHB17-nt275-339 regulatory element. Corn leaf protoplasts were transformed with these plasmids.

TABLE 7

Plasmid, vector and transgene cassette genetic elements link in 5' to 3' direction used to transform corn leaf protoplasts

| Plasmid (EXP) | Annotation | Description |
| --- | --- | --- |
| EXP5-ATHB17ΔA113+ | CaMV.35S duplicated enhancer | Enhancer |
| | Os.Act1 | Promoter |
| | Ta.Lhcb1 | Leader |
| | ATHB17-nt275-339 | Genetic regulatory element (SEQ ID NO:1) in nucleotides 275-339 of ATHB17 coding region |
| | ATHB17ΔA113 | ATHB17Δ113 Coding Sequence (SEQ ID NO:2) |
| | Ta.Hsp17 | 3' UTR |
| EXP5-ATHB17ΔA113- | CaMV.355 duplicated enhancer | Enhancer |
| | Os.Act1 | Promoter |
| | Ta.Lhcb1 | Leader |
| | ATHB17ΔA113 | ATHB17Δ113 Coding Sequence (SEQ ID NO:2) |
| | Ta.Hsp17 | 3' UTR |

Figure 5:
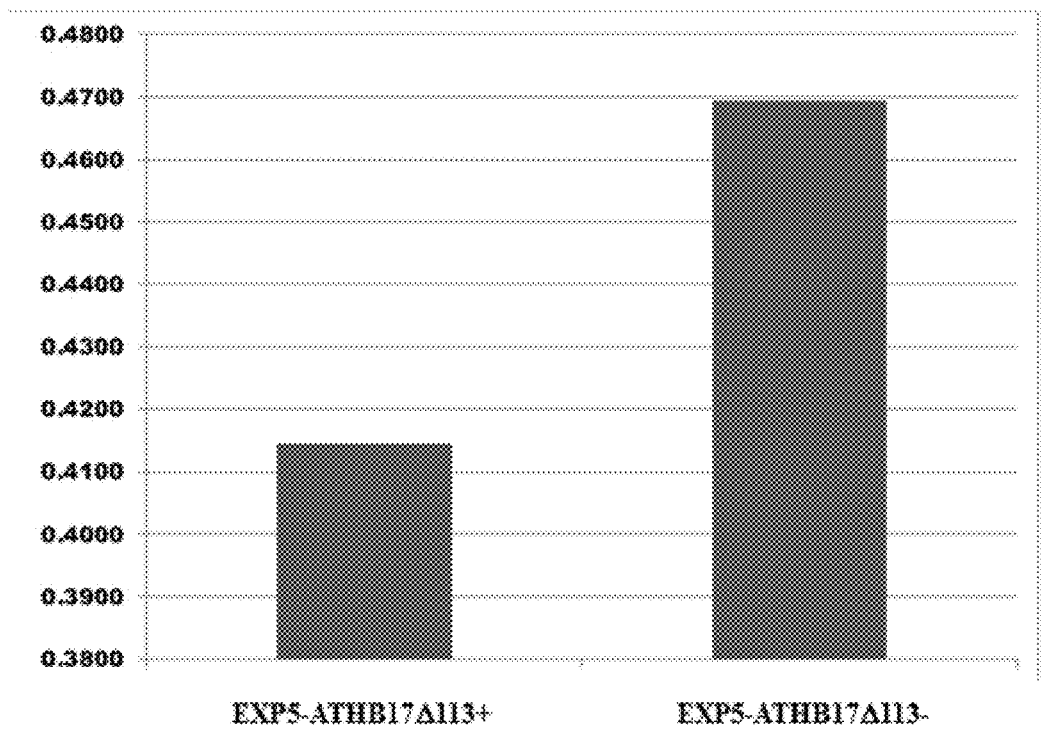
FIG. 5: A graphical representation of the average background subtracted ATHB17Δ113 protein per total protein measured as ng/mg.

Corn leaf protoplasts were transformed using a PEG-based transformation method, as is well known in the art. Protoplast cells were transformed with 0.3 µg/320,000 cells of RLuc Control (described in Example 2 above) plasmid DNA and 5.0 µg/320,000 cells EXP5-ATHB17Δ113+ or EXP5-ATHB17Δ113− and incubated overnight in total darkness. Sample measurements were made using four replicates of each transformation, each replicate sample utilizing 6000 cells. Measurement of ATHB17Δ113 protein for each sample was performed using a standard ELISA assay. A no DNA control was used to assess background. The average background level of the no DNA control was subtracted from each sample derived from transformation with EXP5-ATHB17Δ113+ or EXP5-ATHB17Δ113−. Table 8 below shows the background subtracted levels of ATHB17Δ113 protein expressed as nanogram (ng) ATHB17Δ113 protein per milligram (mg) total protein along with the average of both plasmid constructs. FIG. 5 shows the average background subtracted ng ATHB17Δ113 protein per mg total protein.

TABLE 8

Background subtracted ATHB17Δ113ng protein/mg total protein from samples derived from transformed corn leaf protoplasts

| | Background subtracted ng ATHB17Δ113 /mg total protein | |
| --- | --- | --- |
| | EXP5-ATHB17Δ113+ | EXP5-ATHB17Δ113- |
| Sample 1 | 0.3375 | 0.3762 |
| Sample 2 | 0.4579 | 0.3918 |
| Sample 3 | 0.4486 | 0.5269 |
| Sample 4 | 0.4138 | 0.5829 |
| Average | 0.4144 | 0.4695 |

As can be seen in Table 8 above and FIG. 5, the ATHB17-nt275-339 genetic regulatory element attenuated expression of the ATHB17Δ113 gene in a similar manner as the attenuation of expression observed for GUS and firefly luciferase demonstrated in Examples 2 through 5 above. The ATHB17-nt275-339 genetic regulatory element (SEQ ID NO:1), when operably linked 5' to a protein coding sequence, causes a reduction in protein levels.

Example 7

Redesign of the ATHB17-nt275-339 Genetic Regulatory Element

The ATHB17-nt275-339 genetic regulatory element contains a sequence encoding a start codon at nucleotide positions 25 through 27 of SEQ ID NO:1. This start codon sequence has the potential to cause translation to begin at the start codon sequence of the ATHB17-nt275-339 genetic regulatory element rather than the intended start codon of the 3' operably linked coding sequence. To eliminate this potential issue, the ATHB17-nt275-339 genetic regulatory element was altered by changing the thymine residue at nucleotide position 26 of SEQ ID NO:1 to a cytosine residue; giving rise to a variant regulatory element (SEQ ID NO:4).

To assay the effectiveness of the newly created variant (SEQ ID NO:4) regulatory element, corn plants were transformed with two binary plasmid transformation vectors shown in Table 9 below. The expression cassettes in the vectors in Table 9 had the same expression elements and coding sequence as in the vectors in Table 7 but contained a rice Actin 1 intron operably linked 3' to the wheat Lhcb1 leader, and were binary vectors for Agrobacterium transformation.

TABLE 9

Plant binary transformation vectors used to stably transform corn plants

| Plasmid | Annotation | Description |
| --- | --- | --- |
| EXP6-ATHB17Δ113+ | CaMV.35S duplicated enhancer | Enhancer |
| | Os.Act1 | Promoter |
| | Ta.Lhcb1 | Leader |
| | Os.Act1 | Intron |
| | ATHB17-nt275-339 | Genetic regulatory element (SEQ ID NO: 1) in nucleotides 275-339 of ATHB17 coding region |
| | ATHB17Δ113 | ATHB17Δ113 coding sequence (SEQ ID NO:2) |
| | Ta.Hsp17 | 3' UTR |
| EXP6-ATHB17Δ113+* | CaMV.355 duplicated enhancer | Enhancer |
| | Os.Act1 | Promoter |
| | Ta.Lhcb1 | Leader |
| | Os.Act1 | Intron |
| | variant ATHB17-nt275-339 | Variant Genetic regulatory element (SEQ ID NO:4) |
| | ATHB17ΔA113 | ATHB17Δ113 coding sequence (SEQ ID NO:2) |
| | Ta.Hsp17 | 3' UTR |
| EXP6-ATHB17 | CaMV.355 duplicated enhancer | Enhancer |
| | Os.Act1 | Promoter |
| | Ta.Lhcb1 | Leader |
| | Os.Act1 | Intron |
| | ATHB17 | ATHB17 coding sequence (SEQ ID NO:5) |
| | Ta.Hsp17 | 3' UTR |

All plant binary plasmid transformation vectors shown in Table 9 above were constructed using methods known in the art. The resulting plant expression vectors contained a right border region from Agrobacterium tumefaciens, a transgene cassette comprising an EXP sequence, EXP-CaMV.35S+Os.Act1+Ta.Lhcb1, which consisted of the enhancer element, E-CaMV.35S.2xA1-B3, operably linked 5' to the promoter element, Os.Act1, operably linked 5' to the leader element, Ta.Lhcb1, operably linked 5' to the intron element, Os.Act1, which was operably linked 5' to either the ATHB17-nt275-339 (SEQ ID NO:1) regulatory element or the variant ATHB17-nt275-339 (SEQ ID NO:4) regulatory element, which was operably linked 5' to the ATHB17Δ113 coding sequence (ATHB17Δ113), operably linked 5' to the 3' UTR, Ta.Hsp17, and a left border region of *A. tumefaciens*, and a second transgene cassette used for selection of transformed plant cells that conferred resistance to the herbicide glyphosate (driven by the rice Actin 1 promoter). The resulting vectors were used to transform corn plants.

Plants were transformed using *Agrobacterium*-mediated transformations, for instance as described in U.S. Patent Application Publication 20090138985. Corn plant tissue was transformed with EXP6-ATHB17Δ113+ or EXP6-ATHB17Δ113+* and allowed to regenerate into whole plants. The resulting $R_0$ generation transgenic plants were selected for single copy insertions and allowed to self-cross, resulting in $R_1$ seeds. After analysis of segregation of the $R_1$ plants using methods known in the art, the $R_1$ plants, homozygous for the T-DNA insertion, were self-pollinated to produce $R_2$ seed.

FIG. 6 (further described below in Example 8) shows that EXP6-ATHB17Δ113+ and EXP6-ATHB17Δ113+* produced similar levels of protein.

Example 8

Effect of the ATHB17-nt275-339 Genetic Regulatory Element on ATHB17Δ113 Expression and Phenotypes of Transgenic Inbred Plants in Greenhouse The leader sequence produced as a result of the alternative splicing of the ATHB17 transcript was found critical for regulation of transcription and levels of the translated proteins. To evaluate the impact of the novel leader regulatory sequence, transgenic corn inbred plants comprising the constructs listed in Table 9 in Example 7 and in Table 10 below were evaluated for protein expression and growth phenotypes at different development stages in the greenhouse.

TABLE 10

ATHB17ΔA113 binary transformation vectors without the ATHB17-nt275-339 Genetic Regulatory Element

| Plasmid | Annotation | Description |
| --- | --- | --- |
| EXP7-ATHB17ΔA113- | Os.Act1* | Enhancer |
|  | CaMV.35S duplicated enhancer* | Enhancer |
|  | Os.Act1* | Minimal promoter |
|  | Ta.Lhcb1 | Leader |
|  | Os.Act1 | Intron |
|  | ATHB17ΔA113 | ATHB17ΔA113 coding sequence (SEQ ID NO: 2) |
|  | St.Pis4 | 3' UTR |
| EXP7-ATHB17ΔA113nno- | Os.Act1 | Enhancer |
|  | CaMV.35S enhancer | duplicated Enhancer |
|  | Os.Act1* | Minimal promoter |
|  | Ta.Lhcb1 | Leader |
|  | Os.Act1 | Intron |
|  | ATHB17ΔA113 | ATHB17ΔA113 codingsequence (SEQ ID NO: 2) |
|  | St.Pis4 | 3' UTR |

The three elements marked with a * comprise a 757 bp fragment derived from the rice Actin 1 promoter of EXP6 operably linked 5' to the CaMV 35 duplicated enhancer, that is in turn operably linked 5' to a minimal rice actin 1 promoter consisting of a 80 bp fragment of the rice actin promoter of EXP6 from its 3' end. Basically, in EXP7, the CaMV 35 duplicated enhancer of EXP6 is inserted within the rice actin promoter of EXP6, resulting in the 757 bp fragment being located upstream of the CaMV 35 duplicated enhancer and 80 bp out of 85 bp of the rest of the rice actin promoter of EXP6 being located downstream of the CaMV 35 duplicated enhancer.

Protein Expression in Inbred Transgenic Plants with the ATHB17-nt275-339 Genetic Regulatory Element Each of the events created using the constructs listed in Table 9 was grown in a greenhouse setting side by side. Leaf samples were collected from each at multiple developmental stages (V6, V12, and R1) and evaluated for protein expression using quantitative ATHB17 ELISA assay. The antibody used to develop this ELISA assay was produced against the full length ATHB17 protein, but can detect the full length and truncated (ATHB17Δ113) protein equally well.

Figure 6A:
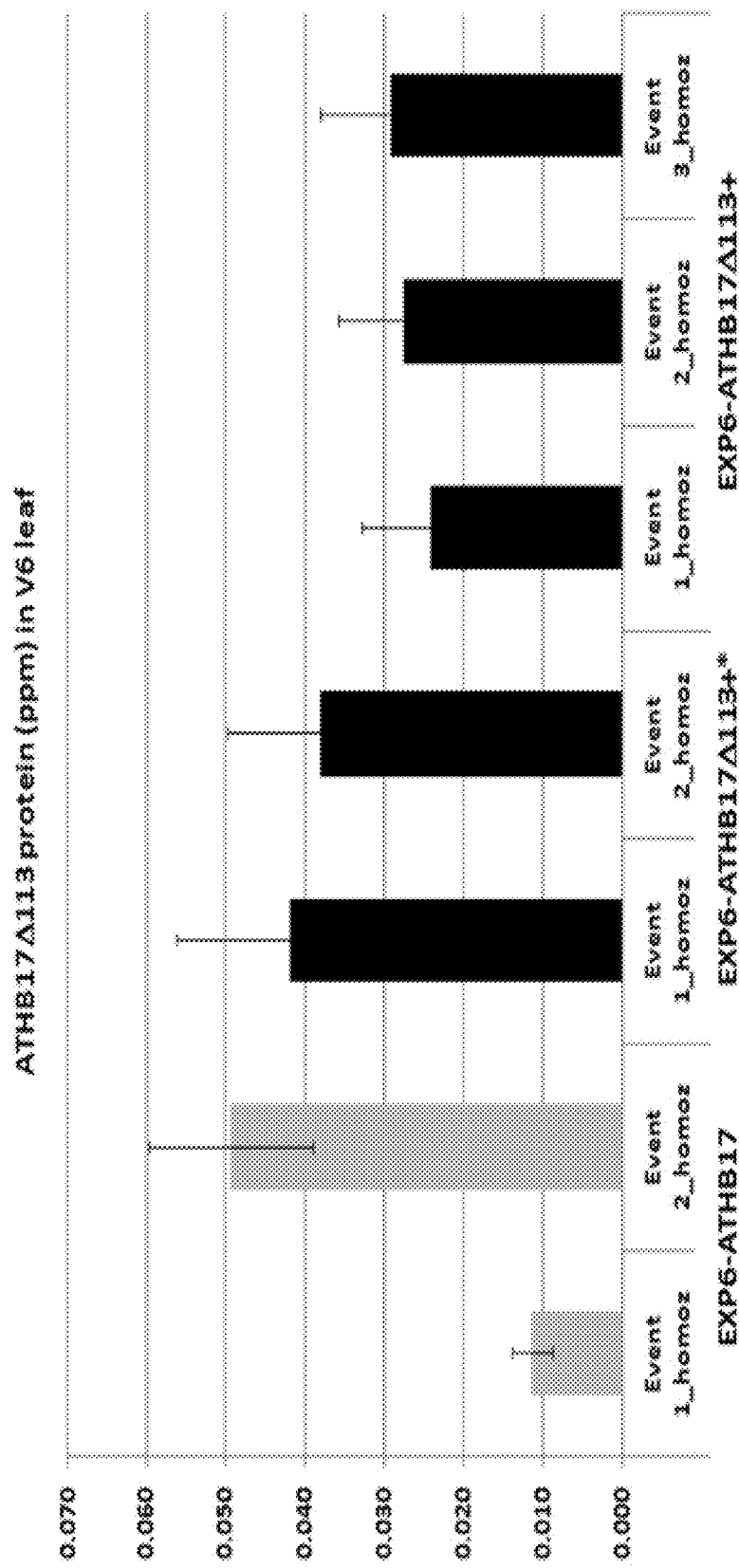
FIGS. 6A-6C: A graphical representation of ATHB17Δ113 protein levels measured in top collared V6 leaf (FIG. 6A), V12 flag and ear leaves (FIG. 6B) and R1 leaf (FIG. 6C) of transgenic inbred plants comprising the ATHB17-nt275-339 and ATHB17Δ113 sequences. Error bars indicate standard deviation. No error bars are included for FIG. 6C as the results are from one plant each. Light grey bars in FIG. 6A indicate that one or more reps in that data set had reported ATHB17Δ113 values below the lower limit of detection of the assay (<0.0084 ppm). "Homoz"=homozygous. "Het"=heterozygous. "Neg seg"=negative segregant.

The protein expression results in the V6 leaf tissue (top collared leaf) are summarized In FIG. 6A. The two ATHB17-nt275-339 sequence-containing constructs (EXP6-ATHB17, EXP6-ATHB17Δ113+ and EXP6-ATHB17 Δ113+*) expressed ATHB17Δ113 protein at similarly low levels, all below 0.1 ppm.

Figure 6B:
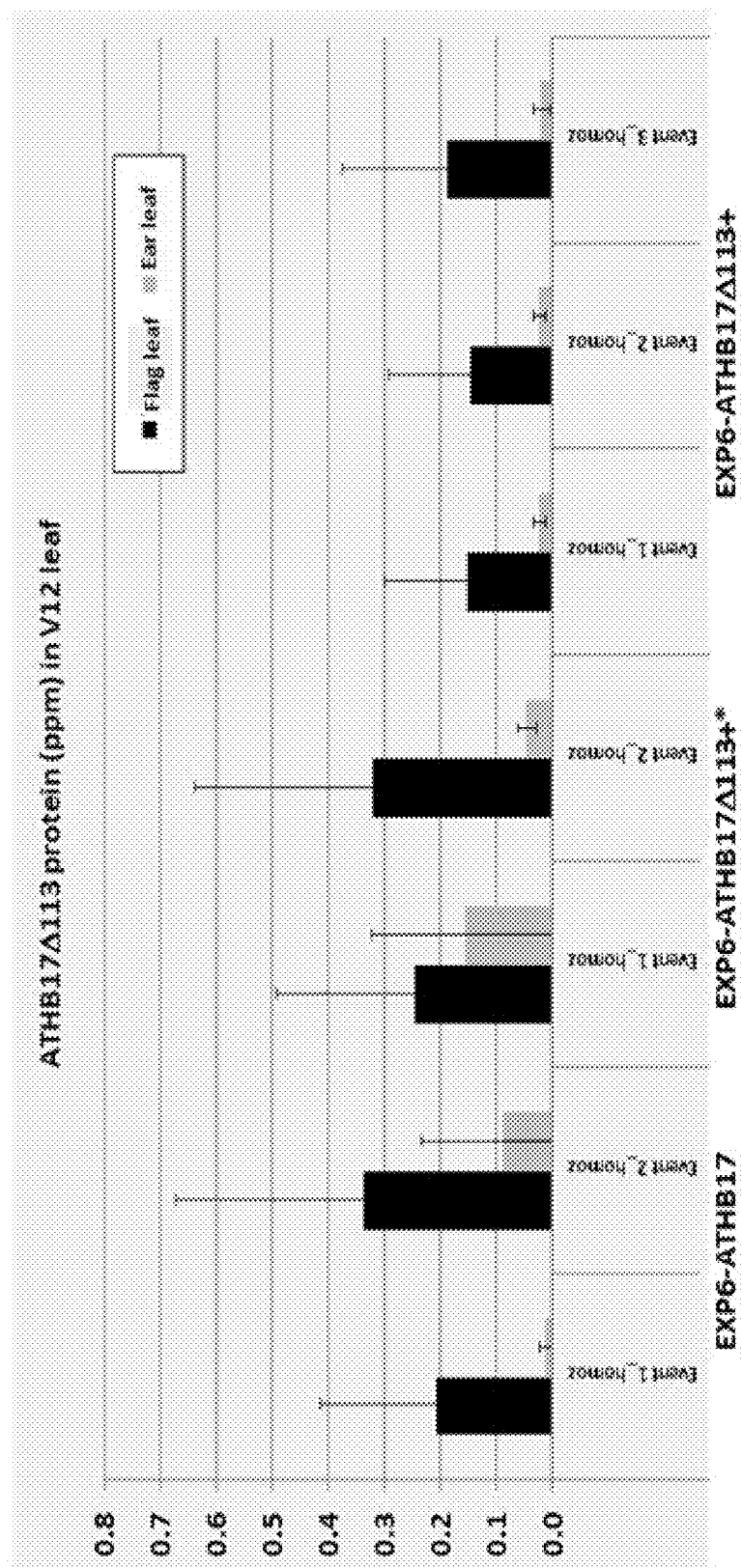

At the V12 stage, samples were taken from the middle portion of the ear leaf and flag leaf. Higher protein expression levels were observed when compared to the levels at V6 stage, with the expression levels generally higher in flag leaves than in ear leaves (FIG. 6B).

At the R1 stage, flag leaves were sampled from plants in three sections as follows:
1. Leaf sheath (the part of the leaf still wrapped around the stem tissue below the leaf);
2. Leaf bottom (bottom four inches of the leaf, includes entire cross-section of leaf at this location, including the unexpected additional growth tissue described earlier), and
3. Leaf middle (cross section of the middle of the leaf).

Figure 6C:
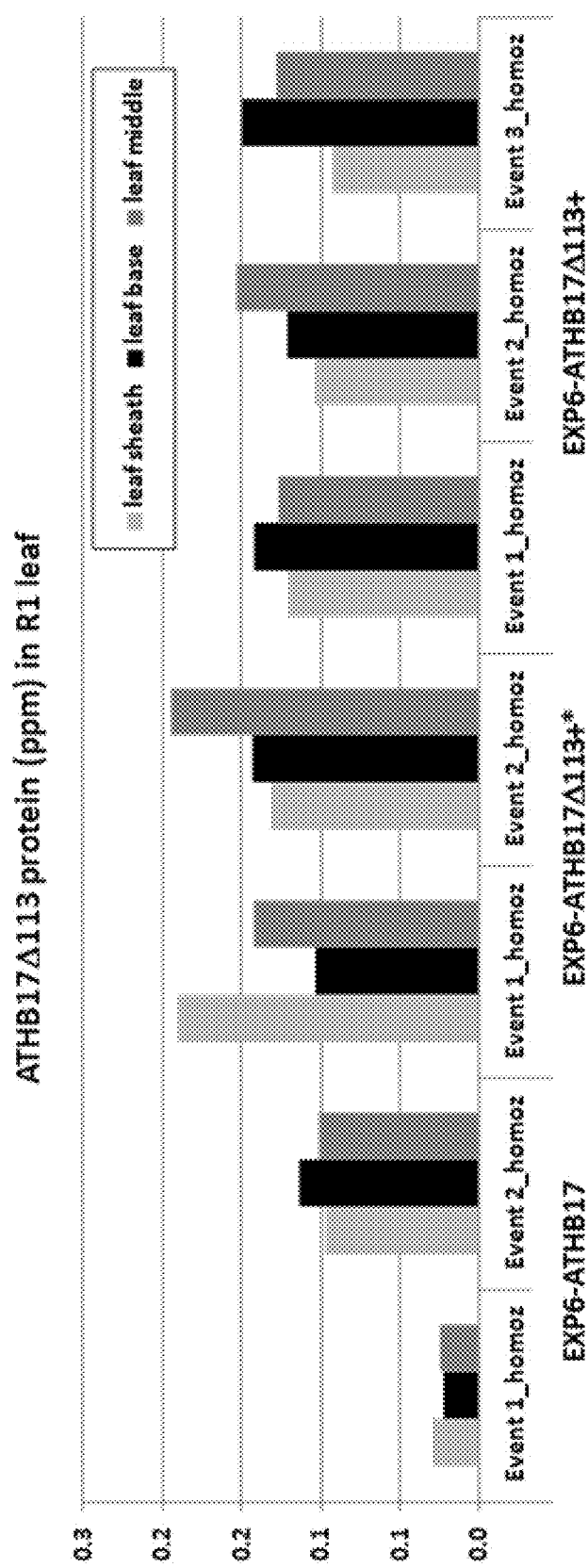

At this stage, ATHB17Δ113 protein levels were either similar to or higher than observed for V6 stage, but lower than observed for V12 stage, with the expression in leaf sheath generally lower than expression in the other two sections of the leaf, but otherwise roughly equivalent expression was observed between the base and middle portions of the leaf (FIG. 6C).

The protein levels observed in V6, V12 and R1 leaves of plants comprising EXP6-ATHB17Δ113+ and EXP6-ATHB17Δ113+* are within the same range of levels detected in the same tissues of plants comprising EXP6-ATHB17. Furthermore, no off-types were observed in these events comprising the ATHB17-nt275-339 genetic regulatory element. In particular, these events did not have the "leaf-on-leaf" off-type observed in events without the ATHB17-nt275-339 genetic regulatory element (as described below).

Protein Expression and Phenotypes of Transgenic Plants without the ATHB17-Nt275-339 Genetic Regulatory Element Transgenic events generated using the constructs without the ATHB17-nt275-339 Genetic Regulatory Element as listed in Table 10 were also tested in a greenhouse along with plants as described in the previous section. As the plants from EXP7-ATHB17Δ113nno- and EXP7-ATHB17Δ113- were from R1 seed sources, these plant populations were all segregating for the gene of interest. Therefore, each of the plants was sampled and assayed for zygosity. Only homozygous positive plants for EXP7-ATHB17Δ113nno− were carried forward for this experiment. For plants transformed with EXP7-ATHB17Δ113−, both homozygous positive and heterozygous plants were carried forward for each event, to allow a comparison of transgene dosage effect. For two events, homozygous negative plants were also carried forward as negative controls. The identities of the transgenes in each event was also verified via PCR and sequencing.

Figure 7A:
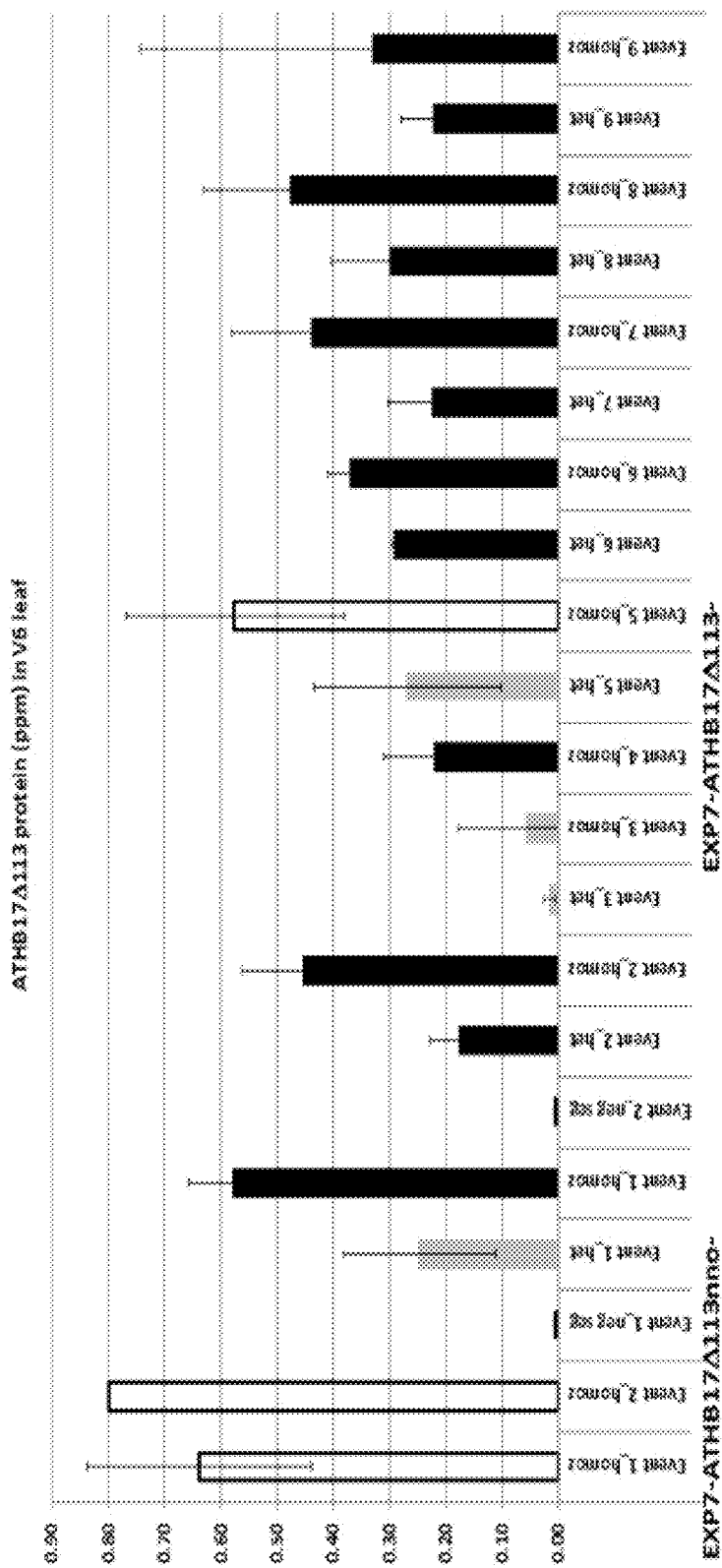
FIGS. 7A-7C: A graphical representation of ATHB17Δ113 protein levels measured in top collared V6 leaf (FIG. 7A), V12 flag and ear leaves (FIG. 7B) and R1 leaf (FIG. 7C) of transgenic inbred plants comprising ATHB17Δ113 without the ATHB17-nt275-339 sequence. Error bars indicate standard deviation. No error bars are included for FIG. 7C as the results are from one plant each. Light grey bars in FIG. 7A indicate that one or more reps in that data set had reported ATHB17Δ113 values below the lower limit of detection of the assay (<0.0084 ppm). Non-filled bars indicate that one or more reps from that event had levels reported above the upper limit of detection for the assay (>0.8 ppm). "Homoz"=homozygous. "Het"=heterozygous. "Neg seg"=negative segregant.

In general, events from these two constructs without the leader sequence (EXP7-ATHB17Δ113− and EXP7-ATHB17Δ113nno−) displayed very high protein levels. At V6 stage, most events showed higher than 0.2 ppm protein, and some expressed the ATHB17Δ113 protein above the upper limit of detection of the assay (0.8 ppm) (FIG. 7A). In general, the heterozygous plants had roughly half as much protein detected as the corresponding homozygotes for the same events, which is expected due to the presence of only one copy of the gene instead of two.

As the plants approached the tasseling stage, an abnormal leaf phenotype was observed in all events from EXP7-ATHB17Δ113− and EXP7-ATHB17Δ113nno−, but not from the negative segregants. This phenotype generally appeared only in the upper leaves of the plants (V12 leaves and up, but in V7 leaves and up for one event), and looked as if an additional leaf, or leaf-like structure, was trying to grow from the midvein of the affected leaves. The higher levels of ATHB17Δ113 protein in these events were believed to impact the meristem tissue formation and growth in these leaves, leading to this "leaf-on-leaf" phenotype.

Figure 7B:
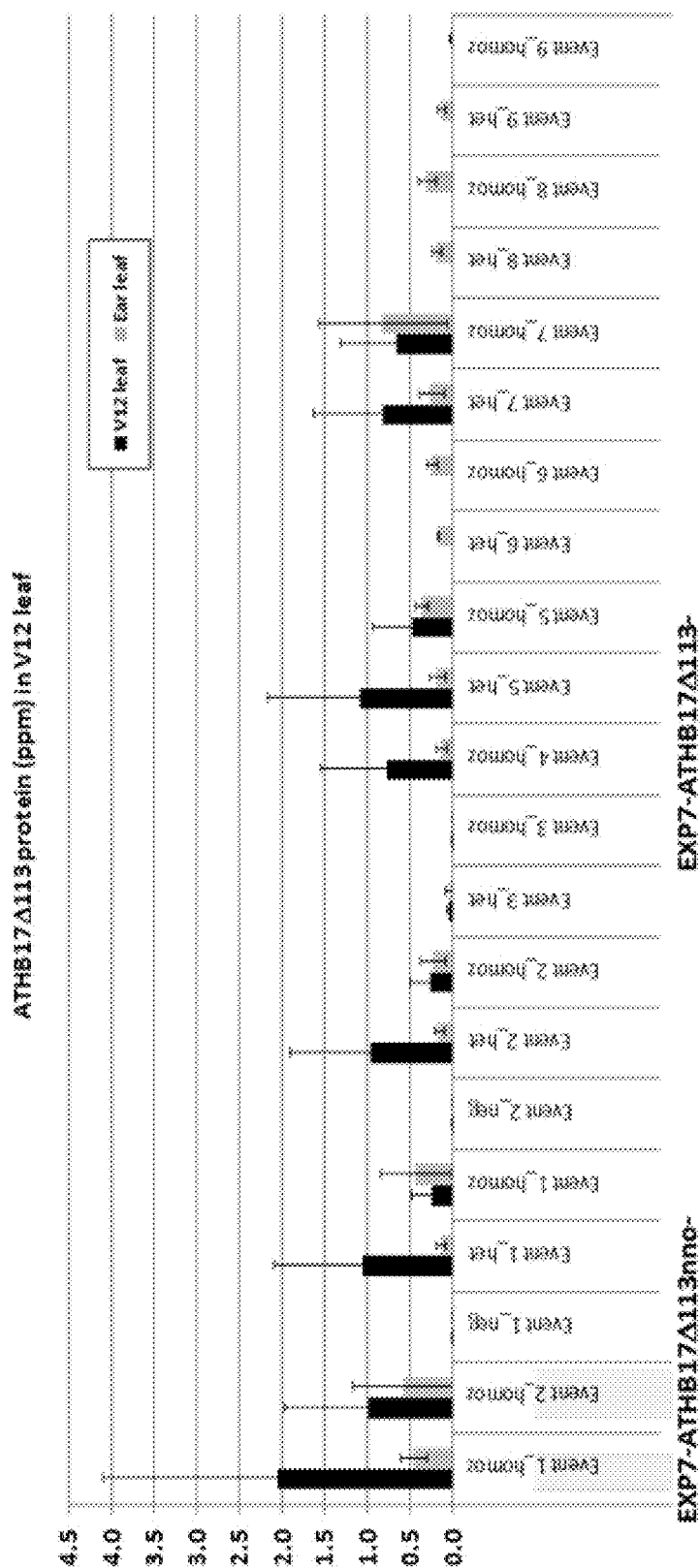

At the V12 stage, the ear leaf samples were collected from the middle portion of the leaf of all events, while the flag leaf samples were taken from some events from the bottom of the leaf that contained the unexpected leaf phenotype. Results of the ELISA analysis from this stage are summarized in FIG. 7B. Generally, much higher protein levels were observed than at the V6 stage, with expression in flag leaves (labeled "V12 leaf" in FIG. 7B) generally higher than expression in the ear leaves. Different dilutions were done for these tissues for the ELISA to allow quantitation of up to 2.0 ppm of ATHB17Δ113 protein. Even so, some events had samples that exceeded this limit.

Figure 7C:
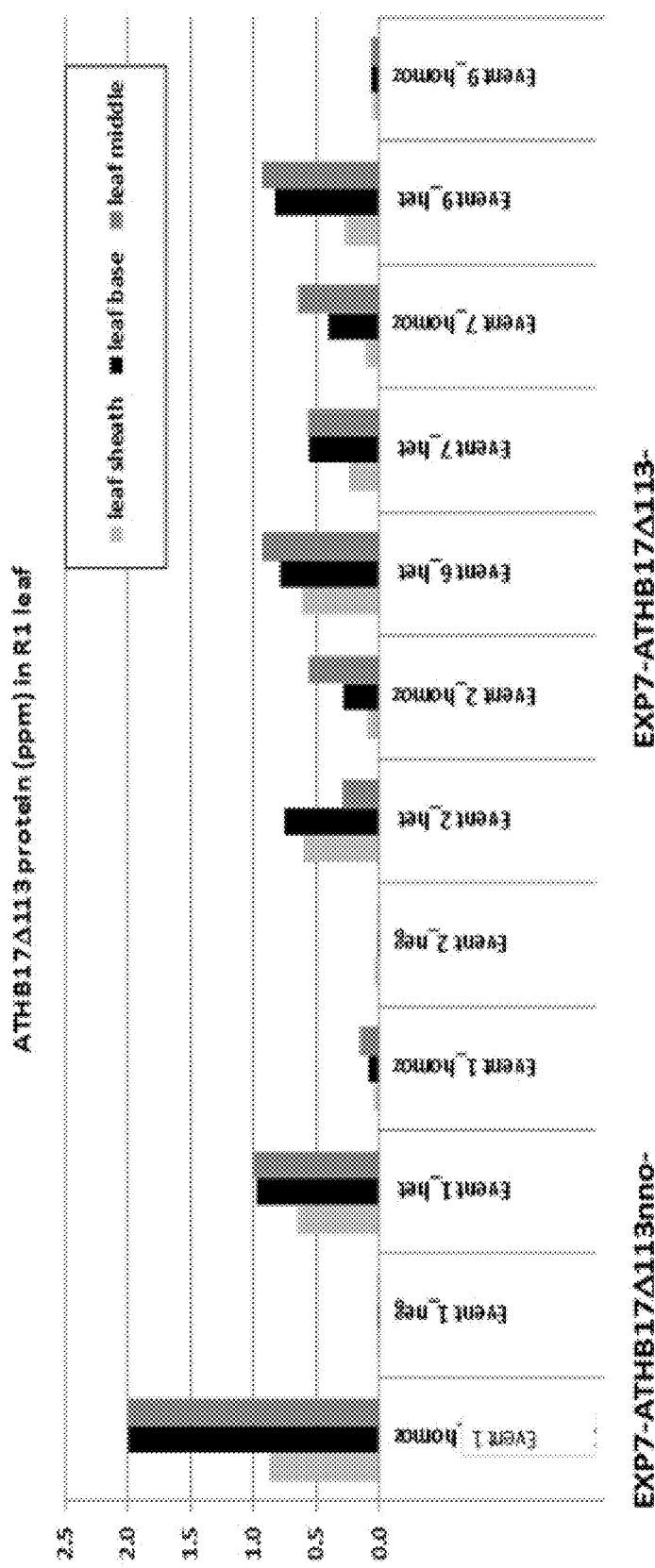

The results of protein expression at R1 stage are shown in FIG. 7C. As in V6 and V12, the protein was expressed at high levels, with the expression in leaf sheath generally lower than expression in the other two sections of the leaf, but otherwise roughly equivalent expression was observed between the base and middle portions of the leaf.

Example 9

Effect of the ATHB17-nt275-339 Genetic Regulatory Element on ATHB17Δ113 Expression and Phenotypes of Transgenic Hybrid Plants in the Field The effect of the ATHB17-nt275-339 genetic regulatory element on RNA and protein expression and phenotypes were assessed for hybrid corn plants grown in the field. The plants comprising different constructs were all in the same hybrid backgrounds.

Figure 8A:
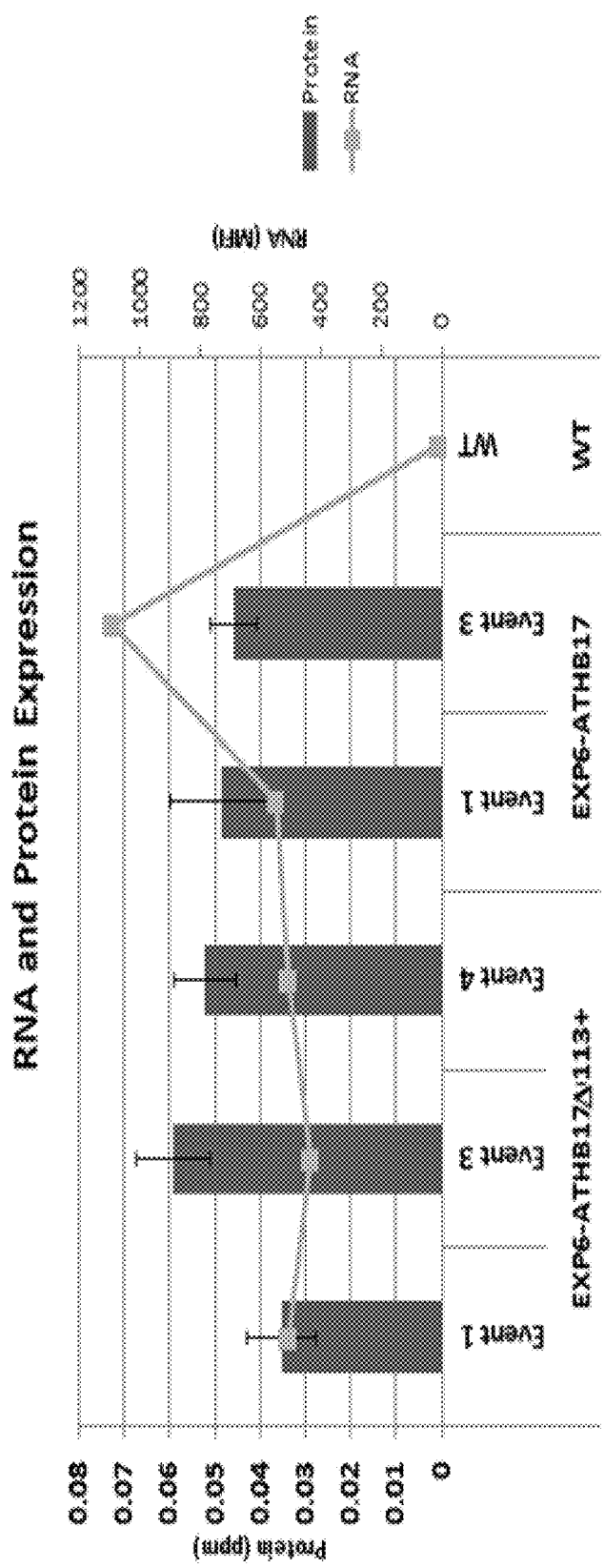
FIGS. 8A-8C: A graphical representation of results from transgenic hybrid corn plants comprising the ATHB17-nt275-339 and ATHB17Δ113 sequences.

Expression and Phenotypes of Transgenic Plants with the ATHB17-nt275-339 Genetic Regulatory Element In one trial, leaf samples were collected from top collared leaves at V6 stage and analyzed for protein and RNA expression. As shown in FIG. 8A, EXP6-ATHB17Δ113+ plants had low levels of protein expression (<0.07 ppm) in the V6 leaves, similar to the levels observed for EXP6-ATHB17 events. In addition, the observed RNA levels correlated with the protein levels.

Figure 8B:
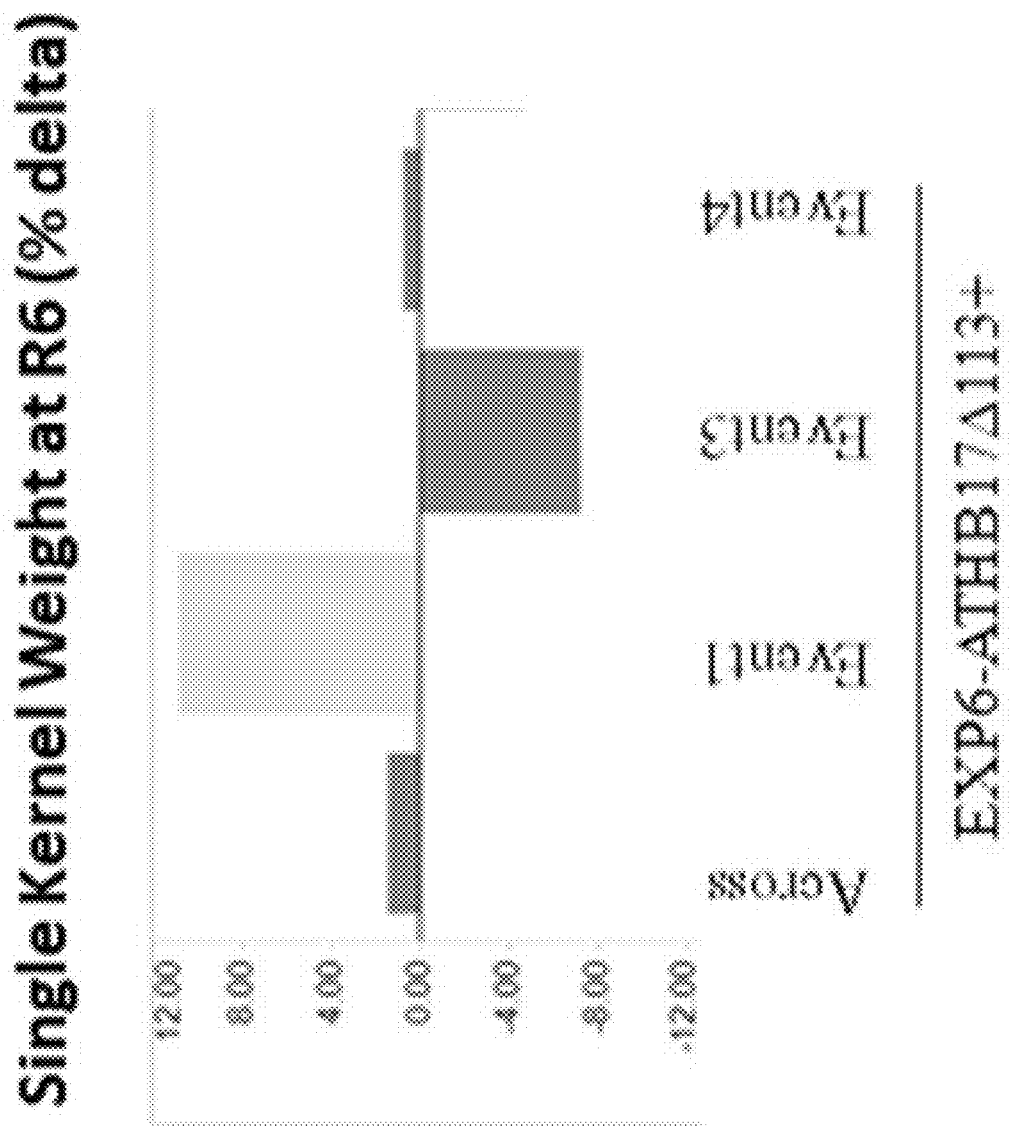

Single kernel weight was measured from the hybrid plants at R6 stage. The results are shown in FIG. 8B. One event showed an increase in single kernel weight at 0.1<p≤0.2, and the other events were neutral.

Figure 8C:
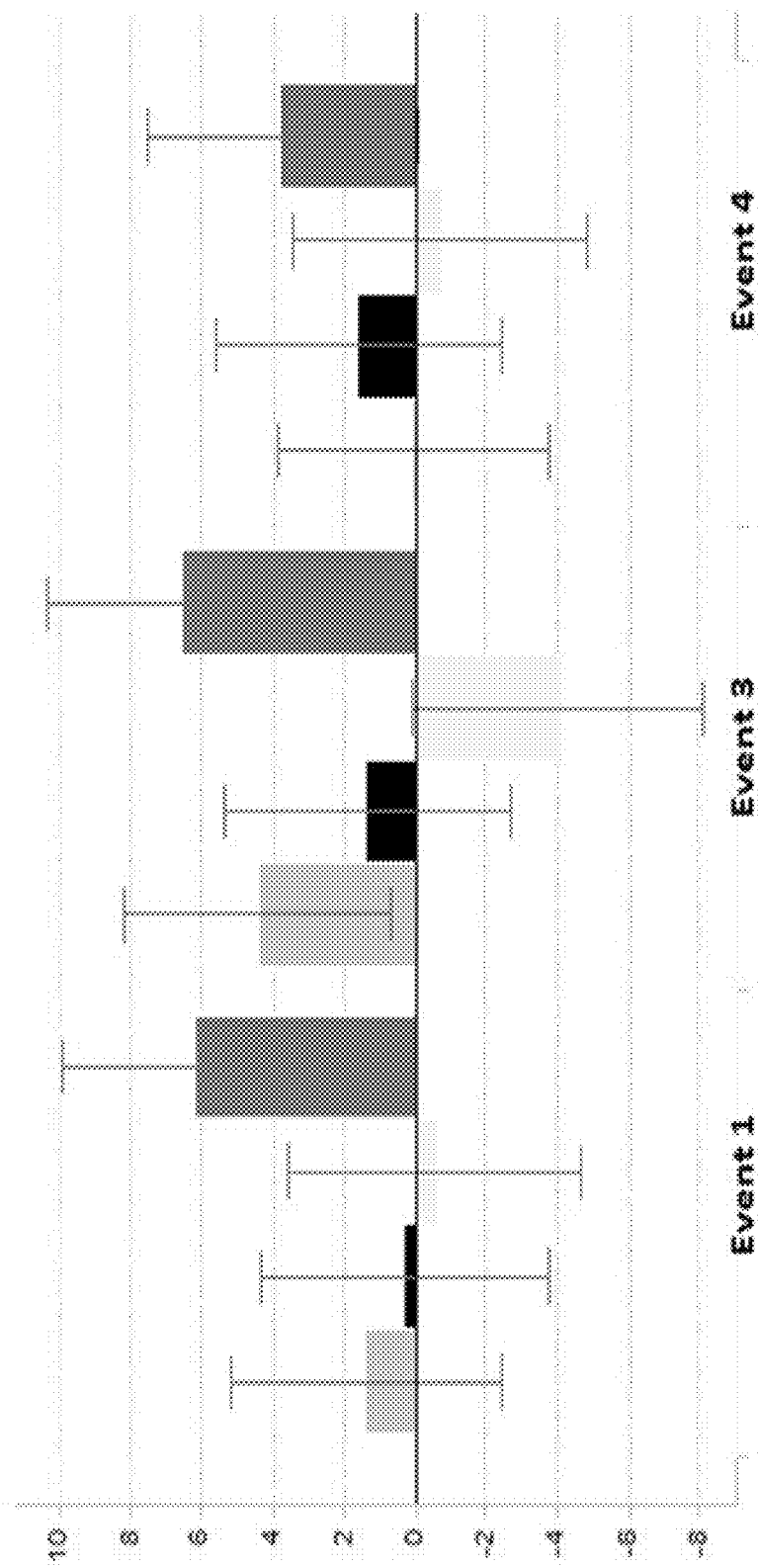

Transgenic corn events comprising these constructs were also tested in different testers for broad acre yield in the field under standard agronomic practices. As shown in FIG. 8C, most EXP6-ATHB17Δ113 events showed positive yield in the four testers tested.

Figure 9A:
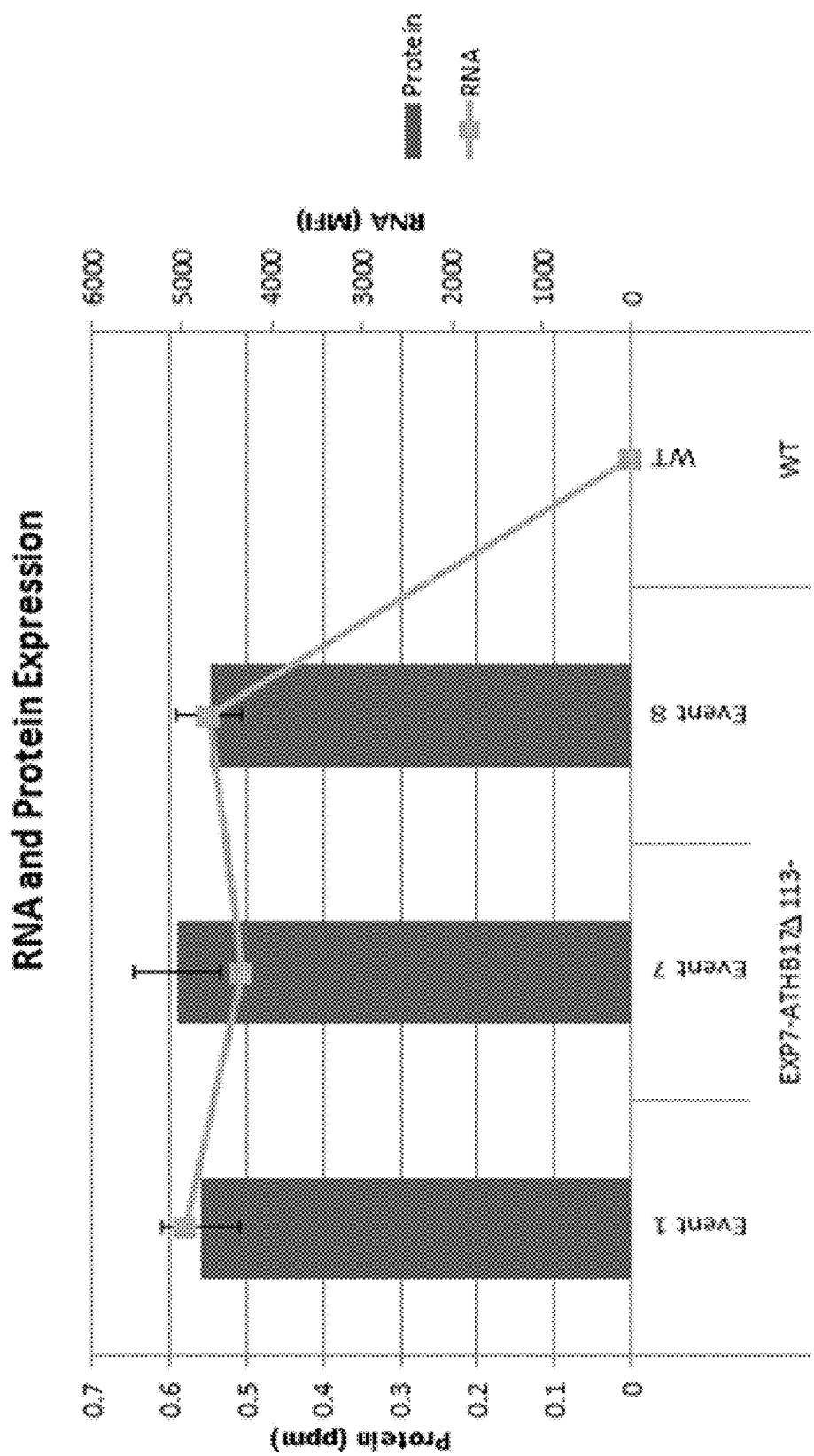
FIGS. 9A-9C: A graphical representation of results from transgenic hybrid corn plants comprising ATHB17Δ113 without the ATHB17-nt275-339 sequence.

Expression and Phenotypes of Transgenic Plants without the ATHB17-Nt275-339 Genetic Regulatory Element Transgenic events generated using the constructs without the ATHB17-nt275-339 genetic regulatory element as listed in Table 10 were also tested for protein and RNA expression along with plants as described in the previous section. Leaf samples were collected from top collared leaves at V6 stage and analyzed for protein and RNA expression. As shown in FIG. 9A, when the ATHB17-nt275-339 genetic regulatory element was absent (EXP7-ATHB17Δ113−), high levels of protein expression were observed (about 0.7 ppm). The result is consistent with the observed protein levels in V6 leaves of inbred plants comprising constructs without the ATHB17-nt275-339 genetic regulatory element grown in the greenhouse. In addition, the RNA levels correlated well with the protein levels (FIG. 9A). However, the leaf-on-leaf phenotype observed in the inbred plants was not detected.

Figure 9B:
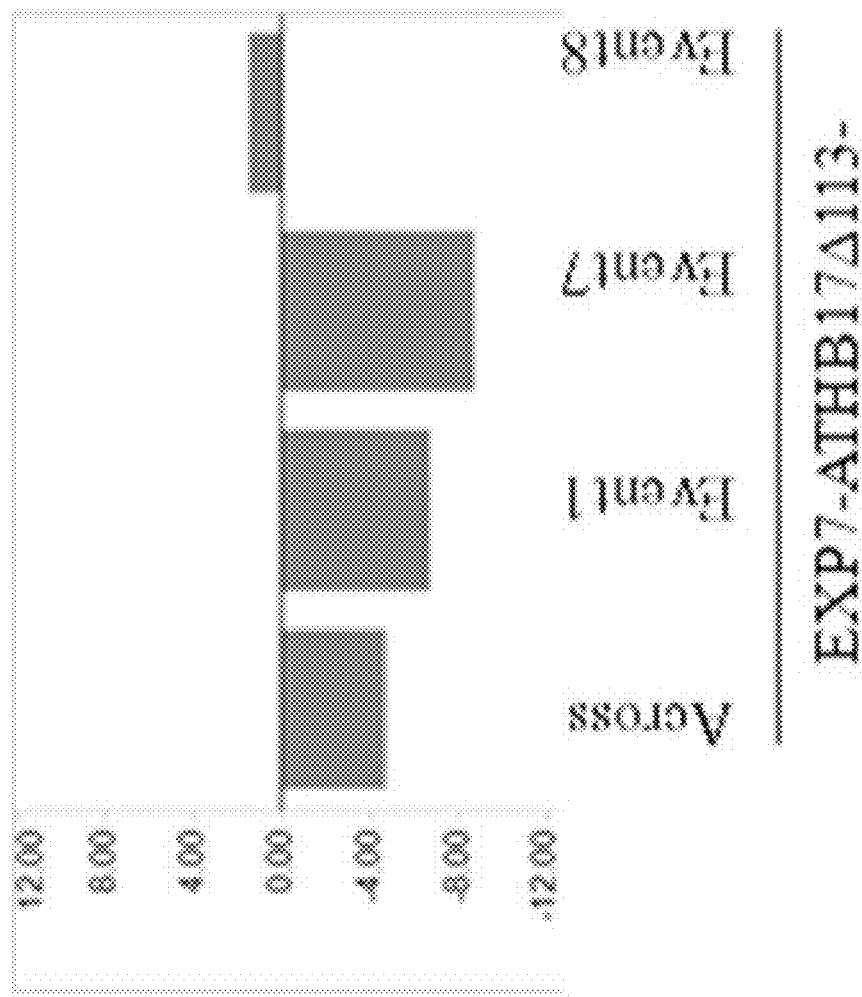

Single kernel weight was also measured from the hybrid plants at R6 stage. As shown in FIG. 9B, most of the events were neutral or trending negative for single kernel weight.

Figure 9C:
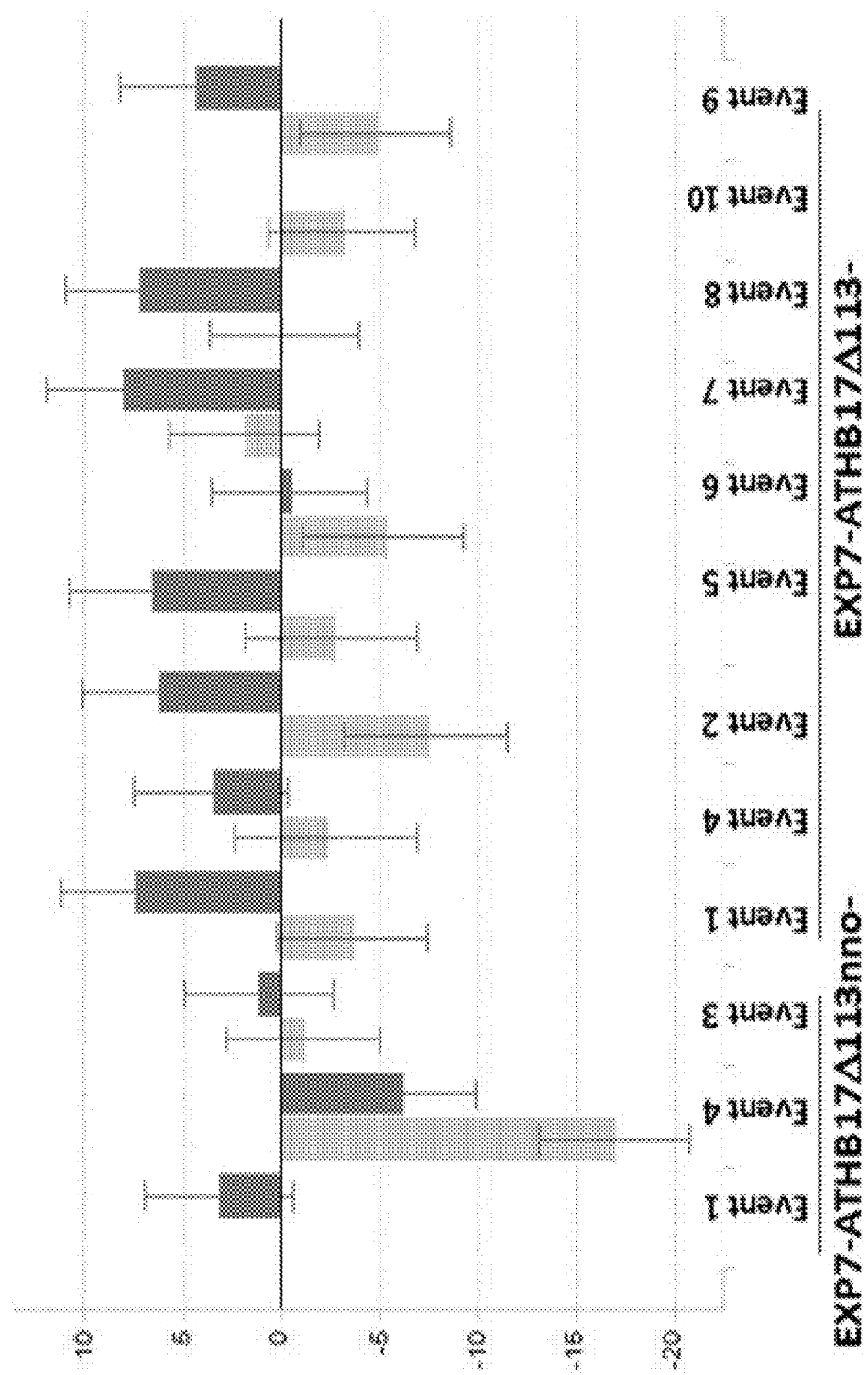

Transgenic corn events comprising the different constructs were also tested in different testers for broad acre yield in the field under standard agronomic practices. As shown in FIG. 9C, some events without the ATHB17-nt275-339 genetic regulatory element showed positive yield in one tester, but negative yield in the other tester. Note that Event 4 comprising EXP7-ATHB17Δ113nno− is a two copy homozygous plant, and Event 10 comprising EXP7-ATHB17Δ113− is a two copy heterozygous plant.

Having illustrated and described the principles of the present disclosure, it should be apparent to persons skilled in the art that the disclosure can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant polynucleotide comprising:
   a) a genetic regulatory element operably linked to a 5' end of a leader regulatory element comprising SEQ ID NO:1 or SEQ ID NO:4 operably linked to a 5' end of a heterologous transcribable polynucleotide, wherein the recombinant polynucleotide lacks nucleotides 1 to 274 of SEQ ID NO:6; or
   b) a genetic regulatory element operably linked to a 5' end of a leader regulatory element comprising SEQ ID NO:1 or SEQ ID NO:4 operably linked to a 5' end of a transcribable polynucleotide, wherein the recombinant polynucleotide lacks nucleotides 1 to 274 of SEQ ID NO:6, wherein the transcribable polynucleotide comprises a sequence encoding the polypeptide of SEQ ID NO:3.

2. The recombinant polynucleotide of claim 1, wherein the leader regulatory element comprises SEQ ID NO:1.

3. The recombinant polynucleotide of claim 1, wherein the leader regulatory element comprises SEQ ID NO:4.

4. A transgenic plant cell comprising the recombinant polynucleotide of claim 1.

5. The transgenic plant cell of claim 4, wherein said transgenic plant cell is a monocotyledonous plant cell.

6. The transgenic plant cell of claim 4, wherein said transgenic plant cell is a dicotyledonous plant cell.

7. A transgenic plant, or part thereof, comprising the recombinant polynucleotide of claim 1.

8. A transgenic seed comprising the recombinant polynucleotide of claim 1.

9. A method of producing a commodity product comprising obtaining the transgenic plant or part thereof according to claim 8 and producing the commodity product therefrom.

10. The method of claim 9, wherein the commodity product is grain, starch, seed, meal, flour, biomass, or seed oil.

11. A method of increasing the yield of a plant comprising expressing in leaf tissue of the plant a recombinant polynucleotide comprising a genetic regulatory element operably linked to a 5' end of a leader regulatory element comprising SEQ ID NO:1 or SEQ ID NO:4 operably linked to a 5' end of a polynucleotide encoding SEQ ID NO:3, wherein the recombinant polynucleotide lacks nucleotides 1 to 274 of SEQ ID NO:6 at a level of from about 0.001 ppm to about 0.5 ppm, wherein the plant lacks leaf-on-leaf off-type.

12. The method of claim 11, wherein the polypeptide is expressed at a level of from about 0.001 ppm to about 0.1 ppm.

13. The method of claim 11, wherein the yield of grain from said plant is increased over the yield of an otherwise isogenic plant not expressing said polypeptide of SEQ ID NO:3.

14. A method for increasing at least one agronomic trait selected from the group consisting of ear biomass, ear size, ear diameter, ear length, kernel size, kernel number per plant, kernel weight or increased grain yield as measured at R6 comprising expressing in V6 leaf tissue of a corn plant a recombinant polynucleotide comprising a genetic regulatory element operably linked to a 5' end of a leader regulatory element comprising SEQ ID NO:1 or SEQ ID NO:4 operably linked to a 5' end of a polynucleotide encoding SEQ ID NO:3, wherein the recombinant polynucleotide lacks nucleotides 1 to 274 of SEQ ID NO:6 at a level of from about 0.001 ppm to about 0.1 ppm.

15. The method of claim 14, wherein at least one agronomic trait is increased over that of an otherwise isogenic plant not expressing said polypeptide of SEQ ID NO:3.

16. A method of obtaining corn seed comprising a transformation event that confers increased ear biomass, ear size, ear diameter, ear length, kernel size, kernel number per plant, kernel weight or increased yield at R6 comprising,
   (a) obtaining a population of corn plants each comprising a transformation event that encodes the polypeptide of SEQ ID NO:3, wherein at least a first member of the population of plants further comprises a recombinant polynucleotide comprising a genetic regulatory element operably linked to a 5' end of a leader regulatory element comprising SEQ ID NO:1 or SEQ ID NO:4 operably linked to a 5' end of a transcribable polynucleotide encoding SEQ ID NO:3, wherein the recombinant polynucleotide lacks nucleotides 1 to 274 of SEQ ID NO:6;

(b) identifying at least a first corn plant that comprises the transformation event that encodes the polypeptide of SEQ ID NO:3, wherein the first corn plant comprises a recombinant polynucleotide comprising a genetic regulatory element operably linked to a 5' end of a leader regulatory element comprising SEQ ID NO:1 or SEQ ID NO:4 operably linked to a 5' end of a transcribable polynucleotide encoding SEQ ID NO:3, wherein the recombinant polynucleotide lacks nucleotides 1 to 274 of SEQ ID NO:6, and expresses the polypeptide of SEQ ID NO:3 in V6 leaf tissue in an amount of from about 0.001 ppm to about 0.1 ppm; and (c) collecting seed from said first corn plant that comprises the transformation event that encodes the polypeptide of SEQ ID NO:3, wherein the first corn plant comprises a recombinant polynucleotide comprising a genetic regulatory element operably linked to a 5' end of a leader regulatory element comprising SEQ ID NO:1 or SEQ ID NO:4 operably linked to a 5' end of a transcribable polynucleotide encoding SEQ ID NO:3, wherein the recombinant polynucleotide lacks nucleotides 1 to 274 of SEQ ID NO:6.

17. A method of producing a transgenic plant comprising: A method for producing transgenic seeds that, when grown, produce plants with increased yield resulting from expression of the recombinant polynucleotide of claim 1, wherein said method comprises:

(a) obtaining a population of transgenic plants comprising a transgene that comprises the recombinant polynucleotide; and (b) collecting seed or a regenerable propagule from said plant.

18. The method of claim 17, further comprising selecting from said population at least a first plant that exhibits increased yield as compared to the yield of an otherwise isogenic control plant.

19. The method of claim 17, further comprising confirming that said transgene is stably integrated in said plant that exhibits increased yield.

20. The method of claim 17, further comprising confirming that said plant expresses the polypeptide sequence of SEQ ID NO:3 at a level of less than about 0.1 ppm in V6 leaf tissue.

21. The method of claim 17, wherein the transgenic plants are corn plants.

22. A method of producing corn grain with increased yield comprising:

(a) planting seeds comprising a recombinant polynucleotide comprising a genetic regulatory element operably linked to a 5' end of a leader regulatory element comprising SEQ ID NO:1 or SEQ ID NO:4 operably linked to a 5' end of a polynucleotide encoding SEQ ID NO:3, wherein the recombinant polynucleotide lacks nucleotides 1 to 274 of SEQ ID NO:6;

(b) cultivating plants and said seeds; and (c) harvesting grain from said plants.

* * * * *

UNITED STATES PATENT AND TRADEMARK OFFICE
CERTIFICATE OF CORRECTION

PATENT NO. : 10,392,626 B1
APPLICATION NO. : 14/511095
DATED : August 27, 2019
INVENTOR(S) : Jeffrey E. Ahrens et al.

Page 1 of 1

It is certified that error appears in the above-identified patent and that said Letters Patent is hereby corrected as shown below:

In the Claims

Column 41, Line 30, please delete "A method of producing a transgenic plant comprising:"

Column 42, Line 30, please delete "( b ) cultivating plants and said seeds; and", and insert
--( b ) cultivating plants from said seeds; and--

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*